US011083722B2

(12) United States Patent
Karr et al.

(10) Patent No.: US 11,083,722 B2
(45) Date of Patent: Aug. 10, 2021

(54) COMBINATION THERAPIES FOR THE TREATMENT OF BREAST CANCER

(71) Applicant: Eisai R&D Management Co., Ltd., Tokyo (JP)

(72) Inventors: Craig D. Karr, Braintree, MA (US); Manav Korpal, Winchester, MA (US); Nathalie Rioux, Woburn, MA (US); Peter Gerard Smith, Arlington, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 113 days.

(21) Appl. No.: 16/493,931

(22) PCT Filed: Mar. 16, 2018

(86) PCT No.: PCT/US2018/022961
§ 371 (c)(1),
(2) Date: Sep. 13, 2019

(87) PCT Pub. No.: WO2018/170447
PCT Pub. Date: Sep. 20, 2018

(65) Prior Publication Data
US 2021/0113537 A1    Apr. 22, 2021

Related U.S. Application Data

(60) Provisional application No. 62/472,345, filed on Mar. 16, 2017.

(51) Int. Cl.
| A61K 31/519 | (2006.01) |
| A61K 31/4427 | (2006.01) |
| A61K 31/415 | (2006.01) |
| A61P 35/00 | (2006.01) |
| A61K 31/445 | (2006.01) |
| A61K 45/06 | (2006.01) |

(52) U.S. Cl.
CPC .......... *A61K 31/445* (2013.01); *A61K 31/519* (2013.01); *A61K 45/06* (2013.01); *A61P 35/00* (2018.01)

(58) Field of Classification Search
CPC .............. A61K 31/519; A61K 31/4427; A61K 31/415; A61P 35/00
USPC .......................... 514/264.1, 265.1, 338, 403
See application file for complete search history.

(56) References Cited

U.S. PATENT DOCUMENTS

| 6,936,612 | B2 | 8/2005 | Barvian et al. |
| 7,208,489 | B2 | 4/2007 | Barvian et al. |
| 7,456,168 | B2 | 11/2008 | Barvian et al. |
| 9,487,530 | B2 | 11/2016 | Strum et al. |
| 9,796,683 | B2 * | 10/2017 | Bock .................... C07D 471/14 |
| 2010/0160340 | A1 | 6/2010 | Coates et al. |
| 2011/0189175 | A1 | 8/2011 | Weinberg et al. |
| 2012/0115878 | A1 | 5/2012 | Calienni et al. |
| 2014/0163052 | A1 | 6/2014 | Chen et al. |
| 2014/0275066 | A1 | 9/2014 | Sharpless et al. |
| 2015/0258080 | A1 | 9/2015 | Hager et al. |
| 2016/0220569 | A1 | 8/2016 | Strum et al. |
| 2016/0347717 | A1 | 12/2016 | Bock et al. |

FOREIGN PATENT DOCUMENTS

| GB | 2483736 | A  | 3/2012 |
| WO | 0044362 | A2 | 8/2000 |
| WO | 0141747 | A2 | 6/2001 |
| WO | 0153293 | A1 | 7/2001 |
| WO | 0153294 | A1 | 7/2001 |
| WO | 0222133 | A1 | 3/2002 |
| WO | 2005012256 | A1 | 2/2005 |
| WO | 2006077424 | A1 | 7/2006 |
| WO | 2006077425 | A1 | 7/2006 |
| WO | 2006077426 | A2 | 7/2006 |
| WO | 2006077428 | A1 | 7/2006 |
| WO | 2007010946 | A1 | 1/2007 |
| WO | 2007124489 | A2 | 11/2007 |
| WO | 2007140222 | A2 | 12/2007 |
| WO | 2008001101 | A2 | 1/2008 |
| WO | 2008007113 | A2 | 1/2008 |
| WO | 2008007122 | A2 | 1/2008 |
| WO | 2008009954 | A1 | 1/2008 |
| WO | 2010020675 | A1 | 2/2010 |
| WO | 2011101417 | A1 | 8/2011 |
| WO | 2011130232 | A1 | 10/2011 |
| WO | 2012061156 | A1 | 5/2012 |
| WO | 2012129344 | A1 | 9/2012 |
| WO | 2014085318 | A1 | 6/2014 |
| WO | 2014144326 | A1 | 9/2014 |
| WO | 2014144847 | A2 | 9/2014 |
| WO | 2015022609 | A1 | 2/2015 |

(Continued)

OTHER PUBLICATIONS

International Search Report (PCT/ISA/210) and Written Opinion (PCT/ISA/237) dated Jun. 4, 2018, by the European Patent Office as the International Searching Authority for International Application No. PCT/US2018/022961.
Leeuwen et al., "Risk of endometrial cancer after tamoxifen treatment of breast cancer", The Lancet, Feb. 1994, vol. 343, p. 448-452.
Shou, et al., "Mechanisms of Tamoxifen Resistance: Increased Estrogen Receptor-HER2/neu Cross-Talk in ER/HER2-Positive Breast Cancer", Journal of the National Cancer Institute, Jun. 2004, vol. 96, No. 12, pp. 926-935.
Fisher, et al., "Tamoxifen for Prevention of Breast Cancer: Report of the National Surgical Adjuvant Breast and Bowel Project P-1 Study", Journal of the National Cancer Institute, Sep. 1998, vol. 90, No. 18, pp. 1371-1388.
Osborne, et al., "Role of the Estrogen Receptor Coactivator AIB1 (SRC-3) and HER-2/neu in Tamoxifen Resistance in Breast Cancer", Journal of the National Cancer Institute, Mar. 2003, vol. 95, No. 5, pp. 353-361.

(Continued)

Primary Examiner — Raymond J Henley, III
(74) Attorney, Agent, or Firm — Buchanan Ingersoll & Rooney PC

(57) ABSTRACT

Provided herein is a combination therapy useful for the treatment breast cancer. The combination comprises an ER-alpha inhibitor and a CDK 4/6 inhibitor.

22 Claims, 9 Drawing Sheets

Specification includes a Sequence Listing.

(56) References Cited

FOREIGN PATENT DOCUMENTS

| WO | 2016025650 A1 | 2/2016 |
| WO | 2016040848 A1 | 3/2016 |
| WO | 2016110224 A1 | 7/2016 |

OTHER PUBLICATIONS

Osborne, et al., "Mechanisms of Endocrine Resistance in Breast Cancer", Annu Rev Med, 2011, vol. 62, pp. 233-247.
Li et al., "Endocrine-therapy-resistant ESR1 variants revealed by genomic characterization of breast-cancer-derived xenografts", Cell Reports, Sep. 2013, vol. 4(6), pp. 1116-1130.
Robinson et al., Activating ESR1 mutations in hormone-resistant metastatic breast cancer, Nat Genet., Dec. 2013. vol. 45(12), pp. 1446-1451.
Toy et al., "ESR1 ligand-binding domain mutations in hormone-resistant breast cancer", Nat Genet., Dec. 2013, vol. 45(12), pp. 1439-1445.
Jeselsohn et al., "Emergence of constitutively active estrogen receptor-alpha mutations in pretreated advanced estrogen receptor-positive breast cancer", Clin Cancer Res., Apr. 2014, vol. 20(7), pp. 1757-1767.
Merenbakh-Lamin et al., "D538G mutation in estrogen receptor-alpha: A novel mechanism for acquired endocrine resistance in breast cancer", Cancer Res., Dec. 2013, vol. 73(23), pp. 6856-6864.
Yu et al., "Cancer therapy. Ex vivo culture of circulating breast tumor cells for individualized testing of drug susceptibility", Science, Jul. 2014, vol. 345, pp. 216-220.
Segal, et al., "Estrogen receptor mutations in breast cancer—new focus on an old target",Clin Cancer Res, Apr. 2014, vol. 20(7), pp. 1724-1726.
Chandarlapaty et al., "Prevalence of ESR1 Mutations in Cell-Free DNA and Outcomes in Metastatic Breast Cancer: A Secondary Analysis of the BOLERO-2 Clinical Trial", JAMA Oncol., Oct. 2016, vol. 2(10), pp. 1310-1315.
Kandoth, et al., "Integrated Genomic Characterization of Endometrial Carcinoma", Nature, May 2013, vol. 497(7447), pp. 67-73.
Finn, et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study", Lancet Oncol 16(1), 2015, pp. 25-35.
O'Leary, et al., "Treating Cancer with Selective CDK 4/6 Inhibitors" Nat. Reviews Clinical Oncology, Jul. 2016, vol. 13, pp. 417-430.
Sorrentino, et al., "G1T38, A Novel, Oral, Potent and Selective CDK 4/6 Inhibitor for the Treatment of RB Competent Tumors", G1 Therapeutics, Inc., Apr. 2016, Abstract #2824, one page.
Bisi, et al., "Preclinical development of G1T38: A novel, potent and selective inhibitor of cyclin dependent kinases 4/6 for use as an oral antineoplastic in patients with CDK4/6 sensitive tumors," Oncotarget, Advance Publications, Mar. 2017, pp. 42343-42358.
Bisi, et al., "Preclinical Characterization of G1T28: A Novel CDK4/6 Inhibitor for Reduction of Chemotherapy-induced Myelosuppression" Mol. Cancer Ther, May 2016, vol. 15(5), pp. 783-793.
Berge et al., Pharmaceutical Salts, J. Pharm. Sci., vol. 66(1), 1977, pp. 1-19.
Coser, et al., "Global analysis of ligand sensitivity of estrogen inducible and suppressible genes in MCF7BUS breast cancer cells by DNA microarray", PNAS, 2003, vol. 100(24), pp. 13994-13999.
Lehár, et al., "Synergistic Drug Combinations Improve Therapeutic Selectivity," Nat Biotechnol., Jul. 2009, vol. 27, No. 7, pp. 659-666.
Rocca, et al., "Palbociclib (PD 0332991): Targeting the Cell Cycle Machinery in Breast Cancer," Expert Opin. Pharmacother., 2014, vol. 15, No. 3, pp. 407-420.

* cited by examiner

COMBINATION THERAPIES FOR THE TREATMENT OF BREAST CANCER

CROSS-REFERENCE TO RELATED APPLICATIONS

This application claims the benefit of U.S. Provisional Patent Application No. 62/472,345, filed on Mar. 16, 2017. That application is incorporated by reference herein.

BACKGROUND

Breast cancer is the most commonly diagnosed malignancy among women today with nearly 200,000/1.7 million new cases diagnosed in the US/worldwide each year respectively. Since about 70% of breast tumors are positive for the estrogen receptor alpha (ERα)—a key oncogenic driver in this subset of tumors (Spicer D V & Pike M C. Breast cancer prevention through modulation of endogenous hormones. *Breast Cancer Res Treat.* 1993; 28: 179-193)-several classes of therapies have been developed to antagonize ERα function, including 1) selective estrogen receptor downregulators (SERDs) of which fulvestrant is an example, 2) selective estrogen receptor modulators (SERMs) of which tamoxifen is an example and 3) aromatase inhibitors that reduce systemic levels of estrogen. These therapies have been largely effective in the clinic reducing occurrence and progression of ERα+ breast tumors. However there are on-target liabilities associated with these different classes of compounds. For example, tamoxifen has been shown to activate signaling activity in the endometrium leading to an increase in risk of endometrial cancers in the clinic (Fisher et al., (1994) *J. Natl Cancer Inst.* April 6; 86(7):527-37; van Leeuwen et al., (1994) *Lancet* February 19; 343(8895):448-52). In contrast, since fulvestrant is a pure antagonist, it can lead to loss of bone density in post-menopausal women as ERα activity is critical for bone building. In addition to on-target side effects, clinical resistance is also beginning to emerge to these classes of ERα antagonists highlighting the need to develop next-generation compounds.

Several mechanisms of resistance have been identified using in vitro and in vivo models of resistance to various endocrine therapies. These include increased ERα/HER2 "crosstalk" (Shou et al., Mechanisms of tamoxifen resistance: increased estrogen receptor-HER2/neu cross-talk in ER/HER2-positive breast cancer (2004) *J Natl Cancer Inst.* June 16; 96(12):926-35), aberrant expression of ERα coactivators/corepressors (Osborne et al., Role of the estrogen receptor coactivator AIB1 (SRC-3) and HER-2/neu in tamoxifen resistance in breast cancer (2003) *J Natl Cancer Inst.* March 5; 95(5):353-61) or loss of ERα altogether to allow ER-independent growth (Osborne C K, Schiff R (2011) *Annu Rev Med* 62: 233-47).

In the hopes of identifying clinically relevant mechanisms of resistance, great effort has also recently gone into deeply characterizing the genetics of endocrine-therapy resistant metastases isolated from patients. Several independent labs have recently published the multitude of genetic lesions observed in the resistant vs the primary tumors (Li et al., Endocrine-therapy-resistant ESR1 variants revealed by genomic characterization of breast-cancer-derived xenografts (2013) *Cell Rep.* September 26; 4(6):1116-30; Robinson et al., Activating ESR1 mutations in hormone-resistant metastatic breast cancer (2013) *Nat Genet.* December; 45(12):1446-51; Toy et al., ESR1 ligand-binding domain mutations in hormone-resistant breast cancer (2013) *Nat Genet.* 2013 December; 45(12):1439-45). Among these are the highly recurrent mutations in the ligand-binding domain of ESR1 (gene which encodes ERα protein) found to be significantly enriched in about 30% of resistant tumors relative to endocrine therapy naïve tumors (Jeselsohn et al., Emergence of constitutively active estrogen receptor-alpha mutations in pretreated advanced estrogen receptor-positive breast cancer (2014) *Clin Cancer Res.* April 1; 20(7):1757-67; Li et al., (2013) *Cell Rep.* September 26; 4(6):1116-30; Toy et al., (2013) *Nat Genet.* 2013 December; 45(12):1439-45; Robinson et al., (2013) *Nat Genet.* December; 45(12):1446-51; Merenbakh-Lamin et al., D538G mutation in estrogen receptor-alpha: A novel mechanism for acquired endocrine resistance in breast cancer (2013) *Cancer Res.* December 1; 73(23):6856-64; Yu et al., Cancer therapy. Ex vivo culture of circulating breast tumor cells for individualized testing of drug susceptibility (2014) *Science* July 11; 345(6193):216-20; Segal and Dowsett Estrogen receptor mutations in breast cancer—new focus on an old target (2014), *Clin Cancer Res* April 1; 20(7):1724-26; Chandarlapaty et al., Prevalence of ESR1 Mutations in Cell-Free DNA and Outcomes in Metastatic Breast Cancer: A Secondary Analysis of the BOLERO-2 Clinical Trial. *JAMA Oncol.* (2016) 2:1310-1315, suggesting the potential for these mutations to functionally drive clinical resistance.

The highly recurrent mutations in the ligand-binding domain of ESR1 are associated with more aggressive disease biology with shorter overall survival relative to the wild-type ESR1 (Chandarlapaty et al., (2016)). Furthermore, ERα mutations (ERα$^{MUT}$) lead to constitutive activation of ERα and confer resistance to existing classes of endocrine therapies. The fact that current endocrine therapies are only partially effective in the ERα$^{MUT}$ setting and since a significant proportion of endocrine-therapy resistant metastases continue to remain dependent on ERα signaling for growth/survival indicates a continuing need to 1) develop the next generation of ERα therapies that can overcome aberrant activities of ERα$^{WT}$/ERα$^{MUT}$ and/or 2) to identify and target cellular pathways that may further enhance the potency of anti-estrogen therapy in the clinic.

Despite advances in the treatment of breast cancer, and particularly ERα positive breast cancer, there is a need to provide improved treatment for breast cancer.

SUMMARY

Embodiments provide a combination therapy, comprising an effective amount of Compound 1 and an effective amount of a CDK4/6 inhibitor. Further embodiments may provide a combination therapy comprising an effective amount of Compound 2 or Compound 3 and an effective amount of a CDK4/6 inhibitor. In certain embodiments the CDK 4/6 inhibitor is palbociclib. In other embodiments the CDK 4/6 inhibitor is ribociclib. In other embodiments the CDK 4/6 inhibitor is abemaciclib. Combination therapy provided herein may lead to an enhanced reduction in the viability of breast cancer cells and may lead to tumor growth inhibition of breast cancer in patients in need of treatment. In certain embodiments the breast cancer cells are ER-positive breast cancer cells.

Embodiments may provide a method of treating breast cancer in a patient in need thereof, including administering to the patient combination of (E)-N,N-dimethyl-4-((2-((5-((Z)-4,4,4-trifluoro-1-(3-fluoro-1H-indazol-5-yl)-2-phenyl-but-1-en-1-yl)pyridin-2-yl)oxy)ethyl)amino)but-2-enamide or a pharmaceutically acceptable salt thereof and a CDK 4/6 inhibitor or a pharmaceutically acceptable salt thereof. In some embodiments the (E)-N,N-dimethyl-4-((2-((5-((Z)-4, 4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof is administered in a daily dosage between 50 mg-1000 mg. In some embodiments the (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof is administered in a daily dosage between 50 mg-500 mg. In some embodiments the (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof is administered in a daily dosage of 50 mg-300 mg.

Embodiments may provide a method of treating breast cancer in a patient in need thereof, including administering to the patient combination of (E)-4-((2-(4-((E)-1-(1H-indazol-5-yl)-2-phenylbut-1-en-1-yl)phenoxy)ethyl)amino)-N,N-dimethylbut-2-enamide or a pharmaceutically acceptable salt thereof and a CDK 4/6 inhibitor or a pharmaceutically acceptable salt thereof. In some embodiments the (E)-4-((2-(4-((E)-1-(H-indazol-5-yl)-2-phenylbut-1-en-1-yl)phenoxy)ethyl)amino)-N,N-dimethylbut-2-enamide or a pharmaceutically acceptable salt thereof is administered in a daily dosage between 50 mg-1000 mg. In some embodiments the (E)-4-((2-(4-((E)-1-(1H-indazol-5-yl)-2-phenylbut-1-en-1-yl)phenoxy)ethyl)amino)-N,N-dimethylbut-2-enamide or a pharmaceutically acceptable salt thereof is administered in a daily dosage between 50 mg-500 mg. In some embodiments the (E)-4-((2-(4-((E)-1-(H-indazol-5-yl)-2-phenylbut-1-en-1-yl)phenoxy)ethyl)amino)-N,N-dimethylbut-2-enamide or a pharmaceutically acceptable salt thereof is administered in a daily dosage of 50 mg-300 mg.

Embodiments may provide a method of treating breast cancer in a patient in need thereof, including administering to the patient combination of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide or a pharmaceutically acceptable salt thereof and a CDK 4/6 inhibitor or a pharmaceutically acceptable salt thereof. In some embodiments the (E)-N,N-dimethyl-4-((2-(4-((E)-4,4,4-trifluoro-1-(3-fluoro-JH-indazol-5-yl)-2-phenylbut-1-en-1-yl)phenoxy)ethyl)amino)but-2-enamide or a pharmaceutically acceptable salt thereof is administered in a daily dosage between 50 mg-1000 mg. In some embodiments the (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide or a pharmaceutically acceptable salt thereof is administered in a daily dosage between 50 mg-500 mg. In some embodiments the (E)-N,N-dimethyl-4-((2-(4-((E)-4,4,4-trifluoro-1-(3-fluoro-/H-indazol-5-yl)-2-phenylbut-1-en-1-yl)phenoxy)ethyl)amino)but-2-enamide or a pharmaceutically acceptable salt thereof is administered in a daily dosage of 50 mg-300 mg.

In some embodiments the CDK 4/6 inhibitor is selected from, for example, 6-acetyl-8-cyclopentyl-5-methyl-2-([5-(piperazin-1-yl)pyridin-2yl]amino)pyrido[2,3-d]pyrimidin-7(8H)-one (palbociclib); 7-Cyclopentyl-2-(5-piperazin-1-yl-pyridin-2-ylamino)-7H-pyrrolo[2,3-d]pyrimidine-6-carboxylic acid dimethylamide (ribociclib); and N-(5-((4-ethylpiperazin-1-yl)methyl)pyridin-2-yl)-5-fluoro-4-(4-fluoro-1-isopropyl-2-methyl-1H-benzo[d]imidazol-6-yl)pyrimidin-2-amine (abemaciclib).

In some embodiments the CDK 4/6 inhibitor is palbociclib. Palbociclib may be administered, for example in a dosage of 75, 100, or 125 mg/day. Typically a dosage is administered orally as a single capsule for 21 consecutive days followed by a 7 day off-treatment period.

In some embodiments the CDK 4/6 inhibitor is ribociclib. Ribociclib may be administered, for example, in a dosage of 200, 400, or 600 mg/day. Typically ribociclib is administered orally as 200 mg capsules or tables, for 21 consecutive days, followed by a 7 day off-treatment period.

In some embodiments the CDK 4/6 inhibitor is abemaciclib. Abemaciclib may be administered, for example, in a dosage of 200, 300, or 400 mg/day. Typically abemaciclib is administered twice-daily in dosages of 100, 150, or 200 mg/dose. Abemaciclib is typically administered for 21 consecutive days or 28 consecutive days, followed by a 7 day off-treatment period.

In some embodiments the CDK 4/6 inhibitor is GT-38 (2'-((5-(4-isopropylpiperazin-1-yl)pyridin-2-yl)amino)-7',8'dihydro-6'H-spiro[cyclohexane-1,9' pyrazino[1',2':1,5]pyrrolo[2,3-d]pyrimidin]-6'-one di-hydrochloride). GIT-38 may be administered, for example, in dosages of 10 mg/kg, 50 mg/kg, 100 mg/kg, 200 mg/kg, 300 mg/kg, 500 mg/kg, or in a range from 10-500 mg/kg or 50-300 mg/kg.

In some embodiments the CDK 4/6 inhibitor is G1T-28 (2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one). G1T-28 may be administered, for example, in dosages of between 190 and 200 mg/m$^2$.

In some embodiments the CDK 4/6 inhibitor is AT-7519. AT-7519 may be administered, for example, in dosages of 14.4 to 32.4 mg/m$^2$. AT-7519 may be dosed every three weeks, with drug given on days 1, 4, 8, and 11. In one embodiment the dose is 27 mg/m$^2$, given at the above frequencies.

In some embodiments the CDK 4/6 inhibitor is FLX-925. In some embodiments the CDK 4/6 inhibitor is alvocidib. Alvocidib may be administered, for example, in amounts between 8 and 122 mg/m$^2$. Alvocidib may be administered as a 72 hour infusion. Maximum tolerated dosages of aovocidib have been reported as 40, 50, or 78 mg/m$^2$.

In some embodiments the (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof and the CDK 4/6 inhibitor or a pharmaceutically acceptable salt thereof are administered as separate formulations. Typically the time between administration of each formulation does not exceed 12 hours. In some embodiments the (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof and the CDK 4/6 inhibitor or a pharmaceutically acceptable salt thereof are administered as a single formulation. In some embodiments the (L)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof and the CDK 4/6 inhibitor or a pharmaceutically acceptable salt thereof are administered sequentially with other treatments. In some embodiments the (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof and the CDK 4/6 inhibitor or a pharmaceutically acceptable salt thereof are administered simultaneously.

In some embodiments the form of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide that is administered is the free base form. In some embodiments the form of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide that is administered is a hydrochloride salt form.

Further embodiments may provide a pharmaceutical formulation including (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof and a CDK 4/6 inhibitor or a pharmaceutically acceptable salt thereof. In some embodiments the (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide is a free base form. In some embodiments the (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide is a hydrochloride salt form.

Further embodiments may provide use of a combination of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof and a CDK 4/6 inhibitor in the treatment of breast cancer. Further embodiments may provide use of a combination of (E)-N,N-dimethyl-4-((2-((5-((Z)-4,4,4-trifluoro-1-(3-fluoro-H-indazol-5-yl)-2-phenylbut-1-en-1-yl)pyridin-2-yl)oxy)ethyl)amino)but-2-enamide or a pharmaceutically acceptable salt thereof and a CDK 4/6 inhibitor in the preparation of a medicament for treatment of breast cancer.

In some embodiments the (E)-4-((2-(4-((E)-1-(1H-indazol-5-yl)-2-phenylbut-1-en-1-yl)phenoxy)ethyl)amino)-N,N-dimethylbut-2-enamide or a pharmaceutically acceptable salt thereof and the CDK 4/6 inhibitor or a pharmaceutically acceptable salt thereof are administered as separate formulations. Typically the time between administration of each formulation does not exceed 12 hours. In some embodiments the (E)-4-((2-(4-((E)-1-(1H-indazol-5-yl)-2-phenylbut-1-en-1-yl)phenoxy)ethyl)amino)-N,N-dimethylbut-2-enamide or a pharmaceutically acceptable salt thereof and the CDK 4/6 inhibitor or a pharmaceutically acceptable salt thereof are administered as a single formulation. In some embodiments the (E)-4-((2-(4-((E)-1-(1H-indazol-5-yl)-2-phenylbut-1-en-1-yl)phenoxy)ethyl)amino)-N,N-dimethylbut-2-enamide or a pharmaceutically acceptable salt thereof and the CDK 4/6 inhibitor or a pharmaceutically acceptable salt thereof are administered sequentially with other treatments. In some embodiments the (E)-4-((2-(4-((E)-1-(H-indazol-5-yl)-2-phenylbut-1-en-1-yl)phenoxy)ethyl) amino)-N,N-dimethylbut-2-enamide or a pharmaceutically acceptable salt thereof and the CDK 4/6 inhibitor or a pharmaceutically acceptable salt thereof are administered simultaneously.

In some embodiments the form of (E)-4-((2-(4-((E)-1-(1H-indazol-5-yl)-2-phenylbut-1-en-1-yl)phenoxy)ethyl) amino)-N,N-dimethylbut-2-enamide that is administered is the free base form. In some embodiments the form (E)-4-((2-(4-((E)-1-(H-indazol-5-yl)-2-phenylbut-1-en-1-yl)phenoxy)ethyl)amino)-N,N-dimethylbut-2-enamide that is administered is a hydrochloride salt form.

Further embodiments may provide a pharmaceutical formulation including (E)-4-((2-(4-((E)-1-(1H-indazol-5-yl)-2-phenylbut-1-en-1-yl)phenoxy)ethyl)amino)-N,N-dimethylbut-2-enamide or a pharmaceutically acceptable salt thereof and a CDK 4/6 inhibitor or a pharmaceutically acceptable salt thereof. In some embodiments the (E)-4-((2-(4-((E)-1-(1H-indazol-5-yl)-2-phenylbut-1-en-1-yl)phenoxy)ethyl) amino)-N,N-dimethylbut-2-enamide is a free base form. In some embodiments the (E)-4-((2-(4-((E)-1-(1H-indazol-5-yl)-2-phenylbut-1-en-1-yl)phenoxy)ethyl)amino)-N,N-dimethylbut-2-enamide is a hydrochloride salt form.

Further embodiments may provide use of a combination of (E)-4-((2-(4-((E)-1-(1H-indazol-5-yl)-2-phenylbut-1-en-1-yl)phenoxy)ethyl)amino)-N,N-dimethylbut-2-enamide or a pharmaceutically acceptable salt thereof and a CDK 4/6 inhibitor in the treatment of breast cancer. Further embodiments may provide use of a combination of (E)-4-((2-(4-((E)-1-(1H-indazol-5-yl)-2-phenylbut-1-en-1-yl)phenoxy)ethyl)amino)-N,N-dimethylbut-2-enamide or a pharmaceutically acceptable salt thereof and a CDK 4/6 inhibitor in the preparation of a medicament for treatment of breast cancer.

In some embodiments the (E)-N,N-dimethyl-4-((2-(4-((E)-4,4,4-trifluoro-1-(3-fluoro-H-indazol-5-yl)-2-phenylbut-1-en-1-yl)phenoxy)ethyl)amino)but-2-enamide or a pharmaceutically acceptable salt thereof and the CDK 4/6 inhibitor or a pharmaceutically acceptable salt thereof are administered as separate formulations. Typically the time between administration of each formulation does not exceed 12 hours. In some embodiments the (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide or a pharmaceutically acceptable salt thereof and the CDK 4/6 inhibitor or a pharmaceutically acceptable salt thereof are administered as a single formulation. In some embodiments the (E)-N,N-dimethyl-4-((2-(4-((E)-4,4,4-trifluoro-1-(3-fluoro-JH-indazol-5-yl)-2-phenylbut-1-en-1-yl)phenoxy) ethyl)amino)but-2-enamide or a pharmaceutically acceptable salt thereof and the CDK 4/6 inhibitor or a pharmaceutically acceptable salt thereof are administered sequentially with other treatments. In some embodiments the (E)-N,N-dimethyl-4-((2-(4-((E)-4,4,4-trifluoro-1-(3-fluoro-H-indazol-5-yl)-2-phenylbut-1-en-1-yl)phenoxy) ethyl)amino)but-2-enamide or a pharmaceutically acceptable salt thereof and the CDK 4/6 inhibitor or a pharmaceutically acceptable salt thereof are administered simultaneously.

In some embodiments the form of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide that is administered is the free base form. In some embodiments the form of (E)-N,N-dimethyl-4-((2-(4-((E)-4,4,4-trifluoro-1-(3-fluoro-JH-indazol-5-yl)-2-phenylbut-1-en-1-yl)phenoxy)ethyl)amino)but-2-enamide that is administered is a hydrochloride salt form.

Further embodiments may provide a pharmaceutical formulation including (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide or a pharmaceutically acceptable salt thereof and a CDK 4/6 inhibitor or a pharmaceutically acceptable salt thereof. In some embodiments the (E)-N,N-dimethyl-4-((2-(4-((E)-4,4,4-trifluoro-1-(3-fluoro-JH-indazol-5-yl)-2-phenylbut-1-en-1-yl)phenoxy)ethyl)amino)but-2-enamide is a free base form. In some embodiments the (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide is a hydrochloride salt form.

Further embodiments may provide use of a combination of (E)-N,N-dimethyl-4-((2-(4-((E)-4,4,4-trifluoro-1-(3-fluoro-1H-indazol-5-yl)-2-phenylbut-1-en-1-yl)phenoxy) ethyl)amino)but-2-enamide or a pharmaceutically acceptable salt thereof and a CDK 4/6 inhibitor in the treatment of breast cancer. Further embodiments may provide use of a combination of (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide or a pharmaceutically acceptable salt thereof and a CDK 4/6 inhibitor in the preparation of a medicament for treatment of breast cancer.

DETAILED DESCRIPTION OF EMBODIMENTS

Figure 1:
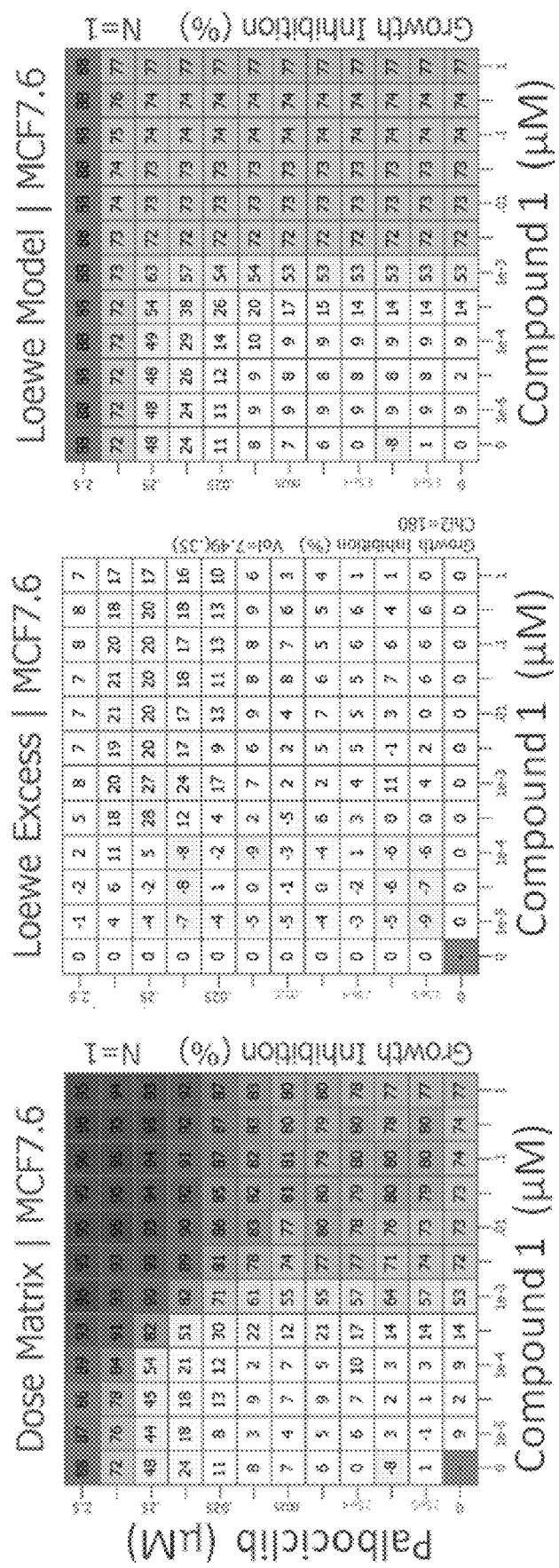
FIG. 1 shows viability of MCF7.6 cells treated for 144 hours with different doses of Compound 1 and palbociclib. Compound 1 and palbociclib synergistically inhibit growth of MCF7.6 cells in vitro. Inhibition of cell viability was measured using CellTiter-Glo, and Chalice software was used to calculate excess inhibition over Loewe additivity for each Compound 1 and palbociclib dose combination.

Provided herein are combination therapies of one or more ER-α inhibitors and one or more CDK 4/6 inhibitors that may be useful in treating breast cancer. In some embodiments, the breast cancer is ER-α+. In embodiments, the breast cancer expresses an ER-α mutation, which may be L536Q (Robinson et al. *Nat Genet.* 2013 December; 45(12)), L536R (Toy et al. *Nat Genet.* 2013 December; 45(12):1439-45), Y537S (Toy et al. *Nat Genet.* 2013 December; 45(12):1439-45; Robinson et al. *Nat Genet.* 2013 December; 45(12); Jeselsohn et al. *Clin Cancer Res.* 2014 April 1; 20(7):1757-67), Y537N (Toy et al. *Nat Genet.* 2013 December; 45(12):1439-45; Jeselsohn et al. *Clin Cancer Res.* 2014 April 1; 20(7):1757-67), Y537C (Toy et al. *Nat Genet.* 2013 December; 45(12):1439-45; Jeselsohn et al. *Clin Cancer Res.* 2014 April 1; 20(7):1757-67) and D538G (Toy et al. *Nat Genet.* 2013 December; 45(12):1439-45; Robinson et al. *Nat Genet.* 2013 December; 45(12); Jeselsohn et al. *Clin Cancer Res.* 2014 April 1; 20(7):1757-67; Merenbakh-Lamin et al. *Cancer Res.* 2013 December 1; 73(23):6856-64), all of which are incorporated by reference in their entireties for their teachings of ER-α mutations.

Thus, the combinations disclosed herein may be also useful for treatment of additional indications and genotypes. ESR1 mutations (Y537C/N) were recently discovered in 4 of 373 cases of endometrial cancers (Kandoth et al. *Nature* 2013 May 2; 497(7447):67-73; Robinson et al. *Nat Genet.* 2013 December; 45(12)). Since it has been shown that ESR1 mutations Y537C/N significantly drive resistance to currently marketed SOC therapies, the compounds disclosed herein may be useful for treating ERα$^{MUT}$ endometrial cancers.

Embodiments as reported herein involve cell cycle inhibition using agents that target cyclin dependent kinases (CDK) 4 and 6 which has recently emerged as an effective approach to prevent and overcome endocrine therapy resistance in metastatic ER-positive breast cancer (Mancuso and Massarweh, Endocrine therapy and strategies to overcome therapeutic resistance in breast cancer. Curr Probl Cancer. 2016; 40: 95-105). In contrast to the enrichment in ESR1 mutations observed in therapy-resistant tumors, mutations in other cancer-related genes failed to show such a robust enrichment strongly implying the importance of ERα mutations in promoting resistance (Jeselsohn et al., (2014) *Clin Cancer Res*. April 1; 20(7):1757-67).

Compound 1 is a small molecule ERα inhibitor with the structure shown in Formula I, and with the chemical name (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide:

(I)

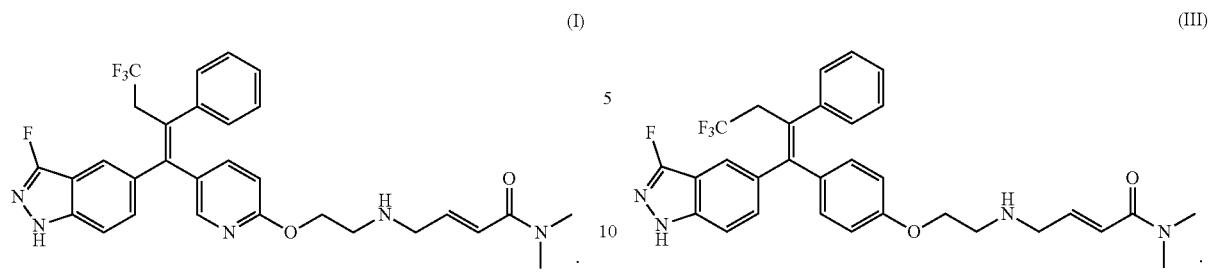

(III)

Compound 1 and its synthesis are reported in United States Patent Application Publication No. US 2016/0347717 A1, published on Dec. 1, 2016. That document is incorporated by reference herein. When used alone or in combinations as described herein, Compound 1 may be administered to patients in any of the following daily dosage amounts: 50 mg-1000 mg; 50 mg-500 mg; 50 mg-300 mg; 50 mg, 100 mg, 200 mg, 300 mg, 500 mg, or 1000 mg. The individual dosage amount may be from 50 mg-1000 mg; 50 mg-500 mg; 50 mg-300 mg; 50 mg, 100 mg, 200 mg, 300 mg, 500 mg, or 1000 mg. The daily dosage may be part of a cyclic regimen. In some embodiments the cyclic regime is one lasting 14 days or 21 days. The daily dosage amount may be administered as a single dosage or as multiple dosages.

Compound 2 is a small molecule ERα inhibitor with the structure shown in Formula II, and with the chemical name (E)-4-((2-(4-((E)-1-(1H-indazol-5-yl)-2-phenylbut-1-en-1-yl)phenoxy)ethyl)amino)-N,N-dimethylbut-2-enamide:

Compound 3 and its synthesis are reported in United States Patent Application Publication No. US 2016/0347717 A1, published on Dec. 1, 2016. Compound 3 may also be used alone or in combinations described herein as treatment for breast cancer, including ERα+ breast cancer. When used alone or in combinations as described herein, Compound 3 may be administered to patients in any of the following daily dosage amounts: 50 mg-1000 mg; 50 mg-500 mg; 50 mg-300 mg; 50 mg, 100 mg, 200 mg, 300 mg, 500 mg, or 1000 mg. The individual dosage amount may be from 50 mg-1000 mg; 50 mg-500 mg; 50 mg-300 mg, 50 mg, 100 mg, 200 mg, 300 mg, 500 mg, or 1000 mg. The daily dosage may be part of a cyclic regimen. In some embodiments the cyclic regime is one lasting 14 days or 21 days. The daily dosage amount may be administered as a single dosage or as multiple dosages.

Palbociclib (6-acetyl-8-cyclopentyl-5-methyl-2-{[5-(piperazin-1-yl)pyridin-2-yl]amino}pyrido[2,3-d]pyrimidin-7(8H)-one) is an FDA-approved inhibitor of cyclin-dependent kinase (CDK) 4 and 6. Palbociclib has the following structure:

(II)

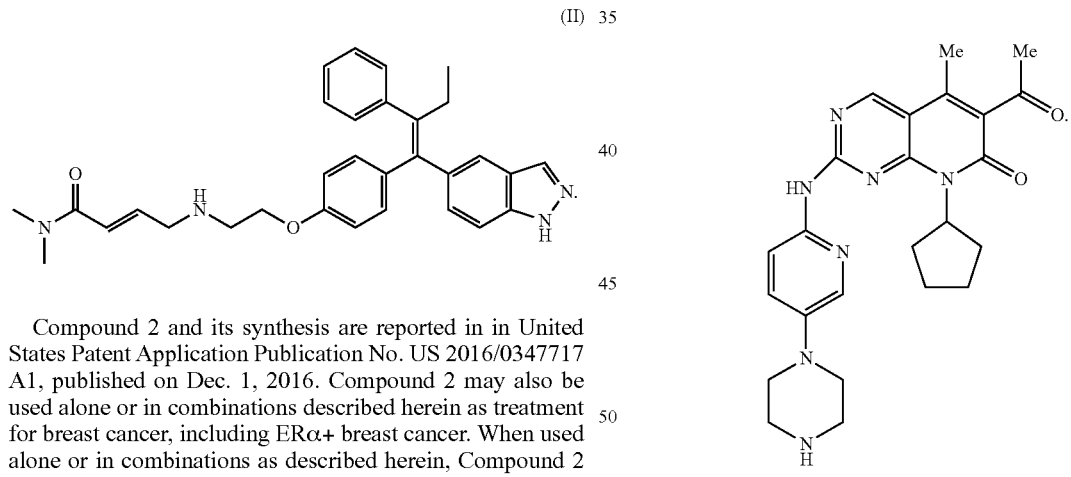

Compound 2 and its synthesis are reported in in United States Patent Application Publication No. US 2016/0347717 A1, published on Dec. 1, 2016. Compound 2 may also be used alone or in combinations described herein as treatment for breast cancer, including ERα+ breast cancer. When used alone or in combinations as described herein, Compound 2 may be administered to patients in any of the following daily dosage amounts: 50 mg-1000 mg; 50 mg-500 mg; 50 mg-300 mg; 50 mg, 100 mg, 200 mg, 300 mg, 500 mg, or 1000 mg. The individual dosage amount may be from 50 mg-1000 mg; 50 mg-500 mg; 50 mg-300 mg; 50 mg, 100 mg, 200 mg, 300 mg, 500 mg, or 1000 mg. The daily dosage may be part of a cyclic regimen. In some embodiments the cyclic regime is one lasting 14 days or 21 days. The daily dosage amount may be administered as a single dosage or as multiple dosages.

Compound 3 is a small molecule ERα inhibitor with the structure shown in Formula III, and with the chemical name (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide:

See U.S. Pat. Nos. 6,936,612; 7,208,489; and 7,456,168, which are incorporated by reference herein. Palbociclib has shown activity in both first- and second-line metastatic disease settings when combined with endocrine therapy leading to significant improvements in PFS suggesting that combination therapy may delay the onset of resistance in patients receiving endocrine therapy (Finn et al., The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study. *Lancet Oncol.* (2015) 16(1): 25-35). Recently, the phase III PALOMA-3 trial also showed significant activity of palbociclib in combination with fulvestrant in patients who progressed on aromatase inhibitor treatment suggesting that the combination may also serve as a viable strategy to overcome resistance to endocrine therapy.

Ribociclib (7-Cyclopentyl-2-(5-piperazin-1-yl-pyridin-2-ylamino)-7H-pyrrolo[2,3-d]pyrimidine-6-carboxylic acid dimethylamide) is an FDA-approved inhibitor of cyclin-dependent kinase (CDK) 4 and 6. Ribociclib has the following structure:

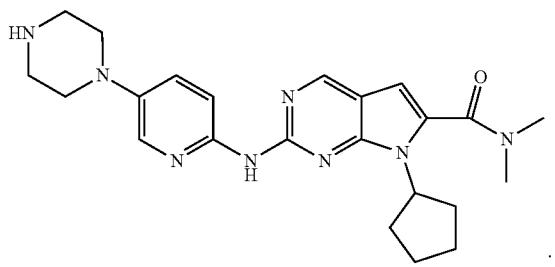 [SMILES: CN(C)C(=O)c1cc2cnc(Nc3ccc(N4CCNCC4)cn3)nc2n1C1CCCC1]

See U.S. Patent App. Pub. No. US20120115878, PCT Publication No. WO2007140222, PCT Publication No. WO2012061156; PCT Publication No. WO2011130232; PCT Publication No. WO2011101417; and PCT Publication No. WO2010020675, all of which are incorporated by reference herein.

Abemaciclib is an inhibitor of CDK 4/6 with the name N-(5-((4-ethylpiperazin-1-yl)methyl)pyridin-2-yl)-5-fluoro-4-(4-fluoro-1-isopropyl-2-methyl-H-benzo[d]imidazol-6-yl)pyrimidin-2-amine. Abemaciclib has the following structure:

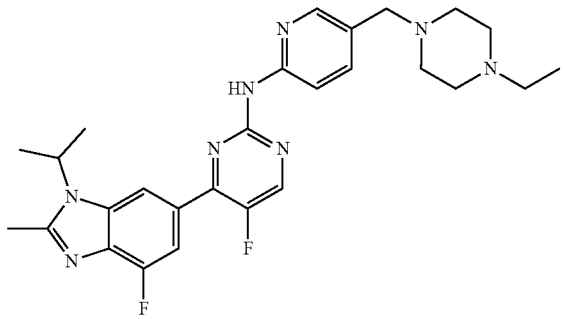

See O'Leary, et al., "Treating Cancer with Selective CDK 4/6 Inhibitors" Nat. Rev. (Published Online Mar. 31, 2016); PCT Publication No. WO2016110224, United States Patent App. Pub. No. 20100160340; and PCT Publication No. WO2016025650, all of which are incorporated by reference herein.

GlT-38 (also referred to as GZ-38-1 or G1T38-1) is a reported inhibitor of CDK 4/6. G1T-38, which is studied by G1 Therapeutics, Inc., of Research Triangle Park, N.C., is reported in Abstract #2824 of the 2016 AACR Annual Meeting, held April 16-20 in New Orleans, La., entitled "G1T38, A Novel, Oral, Potent and Selective CDK 4/6 Inhibitor for the Treatment of RB Competent Tumors," by J. Sorrentino, J. Bisi, P. Roberts, and J. Strum. that document is incorporated by reference herein. GIT38 has the chemical name 2'-((5-(4-isopropylpiperazin-1-yl)pyridin-2-yl)amino)-7',8'dihydro-6'H-spiro[cyclohexane1,9' pyrazino[1',2':1,5] pyrrolo[2,3-d]pyrimidin]-6'-one di-hydrochloride, and the structure set forth below:

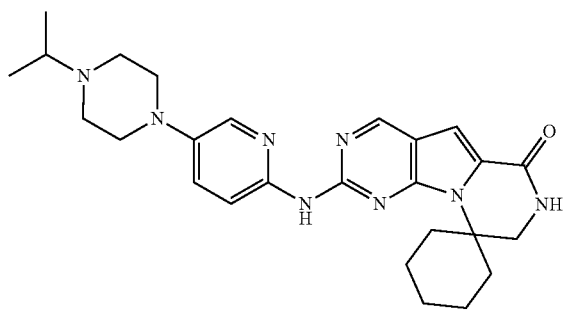 [SMILES: CC(C)N1CCN(c2ccc(Nc3ncc4cc5n(c4n3)C3(CCCCC3)CNC5=O)nc2)CC1]

See Bisi, et al., "Preclinical development of G1T38: A novel, potent and selective inhibitor of cyclin dependent kinases 4/6 for use as an oral antineoplastic in patients with CDK4/6 sensitive tumors," Oncotarget, Advance Publications 2017 (Mar. 15, 2017); U.S. Patent App. Pub. No. US 20140275066 A1; U.S. Pat. No. 9,487,530 B2; and PCT International Patent Application Pub. No. WO 2014144326, all of which are incorporated by reference herein.

G1T-28 (also referred to as trilaciclib) is an inhibitor of CDK 4/6 with the name 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one. G1T-28 has the following structure:

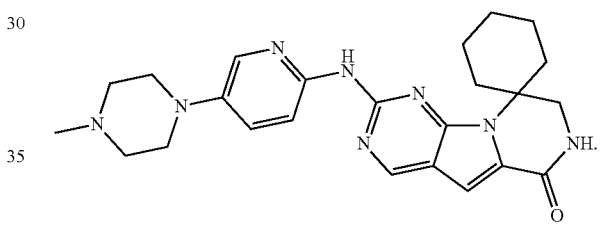

See, for example, Bisi, et al., "Preclinical Characterization of GT28: A Novel CDK4/6 Inhibitor for Reduction of Chemotherapy-induced Myelosuppression" Mol. Cancer Ther.; 15(5) 783-93, May 2016; U.S. Patent Application Publication No. US20160220569; PCT International Patent Application Publication Nos. WO2014144326; WO2014144847; and WO2016040848, all of which are incorporated by reference herein.

AT-7519 is an inhibitor of CDK 4/6 with the name N-(4-piperidinyl)-4-(2,6-dichlorobenzoylamino)-1H-pyrazole-3 carboxamide. AT-7519 has the following structure:

See, for example, PCT International Patent Application Publication Nos. WO 2005012256; WO 2006077424; WO 2006077426; WO 2008001101, WO 2006077425; WO 2006077428; WO 2008007113: WO 2008007122; and WO 2008009954, which are incorporated by reference herein.

FLX-925 (also known as AMG-925) is an inhibitor of CDK 4/6 with the name 2-Hydroxy-1-[2-[[9-(trans-4-methylcyclohexyl)-9H-pyrido[4',3':4,5]pyrrolo[2,3-d]pyrimidin- 2-yl]amino]-7,8-dihydro-1,6-naphthyridin-6(5H)-yl]ethanone. FLX-925 has the following structure:

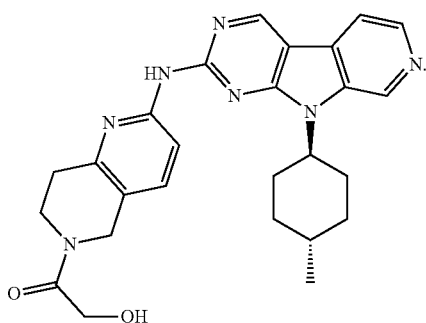 [SMILES: C[C@H]1CC[C@H](n2c3cnccc3c3cnc(Nc4ccc5c(n4)CCN(C(=O)CO)C5)nc32)CC1]

See, for example, U.S. Patent Application Pub. No. 2014163052 and PCT International Patent Application Publication No. WO 2012129344, both of which are incorporated by reference herein.

Alvocidib is an inhibitor of CDK 4/6 with the name 2-(2-chlorophenyl)-5,7-dihydroxy-8-((3S,4R)-3-hydroxy-1-methylpiperidin-4-yl)-4H-chromen-4-one. Alvocidib has the following structure:

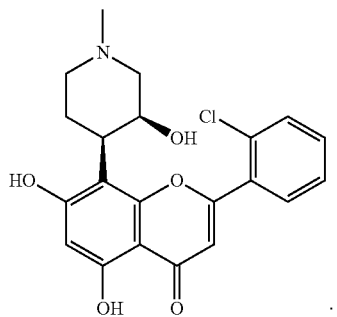 [SMILES: CN1CC[C@H](c2c(O)cc(O)c3c(=O)cc(-c4ccccc4Cl)oc23)[C@H](O)C1]

See, for example, U.S. Patent Application Publication No. US2011189175 and US2011189175; PCT International Patent Application Publication Nos. WO 2000044362; WO 2001041747; WO 2001053293; WO 2001053294; WO 2002022133; WO 2007010946, all of which are incorporated by reference herein.

In some embodiments, the combination therapies include administration of Compound 1 in combination with a CDK 4/6 inhibitor. In certain embodiments the CDK 4/6 inhibitor is palbociclib. In other embodiments, the CDK 4/6 inhibitor is ribociclib. In still other embodiments the CDK 4/6 inhibitor is abemaciclib. In still other embodiments the CDK 4/6 inhibitor is G1T-38. In further embodiments the CDK 4/6 inhibitor is trilaciclib. In still other embodiments the CDK 4/6 inhibitor is AT-7519. In further embodiments the CDK 4/6 inhibitor is FLX-925. In further embodiments the CDK 4/6 inhibitor is alvocidib.

Provided herein are combinations of therapeutic agents and methods for administration of the combination of agents to treat breast cancer. As used herein, a "combination of therapeutic agents" and similar terms refer to a combination of two types of therapeutic agents: (1) Compound 1 and/or pharmacologically active salts thereof and (2) a CDK 4/6 inhibitor, and/or pharmacologically active salts thereof. "Combination" as used herein (including in the term "combination of therapeutic agents") refers to these types of therapeutic agents co-formulated in a single dosage form, individually formulated and co-administered, or individually formulated and sequentially administered.

Compound 1 is a small molecule ERα inhibitor with the structure shown in Formula I, and with the chemical name (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide:

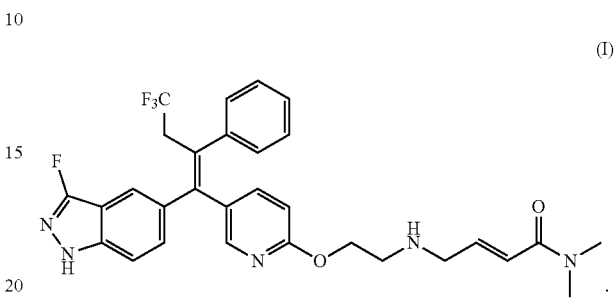

(I)

Compound 1 and its synthesis are reported in United States Patent Application Publication No. US 2016/0347717 A1, published on Dec. 1, 2016. That document is incorporated by reference herein. Compound 1 may also be used alone or in combinations described herein as treatment for breast cancer, including ERα+ breast cancer. When used alone or in combinations as described herein, Compound 1 may be administered to patients in any of the following daily dosage amounts: 50 mg-1000 mg; 50 mg-500 mg; 50 mg-300 mg; 50 mg, 100 mg, 200 mg, 300 mg, 500 mg, or 1000 mg. The individual dosage amount may be from 50 mg-1000 mg; 50 mg-500 mg; 50 mg-300 mg; 50 mg, 100 mg, 200 mg, 300 mg, 500 mg, or 1000 mg. The daily dosage may be part of a cyclic regimen. In some embodiments the cyclic regime is one lasting 14 days or 21 days. The daily dosage amount may be administered as a single dosage or as multiple dosages.

Compound 2 is a small molecule ERα inhibitor with the structure shown in Formula II, and with the chemical name (E)-4-((2-(4-((E)-1-(H-indazol-5-yl)-2-phenylbut-1-en-1-yl)phenoxy)ethyl)amino)-N,N-dimethylbut-2-enamide:

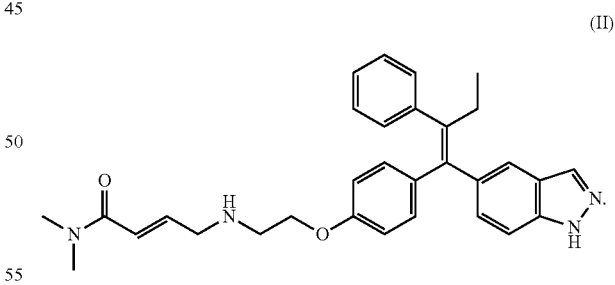

(II)

Compound 2 and its synthesis are reported in United States Patent Application Publication No. US 2016/0347717 A1, published on Dec. 1, 2016. Compound 2 may also be used alone or in combinations described herein as treatment for breast cancer, including ERα+ breast cancer. When used alone or in combinations as described herein, Compound 2 may be administered to patients in any of the following daily dosage amounts: 50 mg-1000 mg; 50 mg-500 mg; 50 mg-300 mg; 50 mg, 100 mg, 200 mg, 300 mg, 500 mg, or 1000 mg. The individual dosage amount may be from 50 mg-1000 mg; 50 mg-500 mg; 50 mg-300 mg; 50 mg, 100 mg, 200 mg, 300 mg, 500 mg, or 1000 mg. The daily dosage may be part of a cyclic regimen. In some embodiments the cyclic regime is one lasting 14 days or 21 days. The daily dosage amount may be administered as a single dosage or as multiple dosages.

Compound 3 is a small molecule ERα inhibitor with the structure shown in Formula III, and with the chemical name (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide:

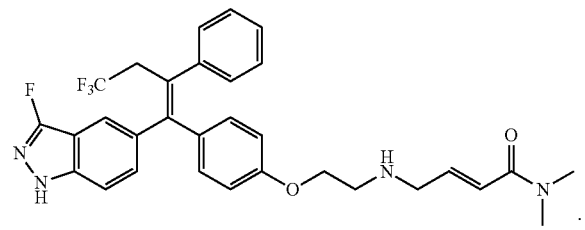

(III)

Compound 3 and its synthesis are reported in United States Patent Application Publication No. US 2016/0347717 A1, published on Dec. 1, 2016. That document is incorporated by reference herein. Compound 3 may also be used alone or in combinations described herein as treatment for breast cancer, including ERα+ breast cancer. When used alone or in combinations as described herein, Compound 3 may be administered to patients in any of the following daily dosage amounts: 50 mg-1000 mg; 50 mg-500 mg; 50 mg-300 mg; 50 mg, 100 mg, 200 mg, 300 mg, 500 mg, or 1000 mg. The individual dosage amount may be from 50 mg-1000 mg; 50 mg-500 mg; 50 mg-300 mg; 50 mg, 100 mg, 200 mg, 300 mg, 500 mg, or 1000 mg. The daily dosage may be part of a cyclic regimen. In some embodiments the cyclic regime is one lasting 14 days or 21 days. The daily dosage amount may be administered as a single dosage or as multiple dosages.

CDK 4/6 inhibitors suitable for use herein may include, for example, ribociclib, palbociclib, and abemaciclib, G1T-38, trilaciclib, AT-7519, FLX-925, and alvocidib, and their pharmaceutically acceptable salts and hydrates.

Administration of a combination of therapeutic agents comprises administration of the individual therapeutic agents in combination in a single formulation or unit dosage form, administration of the individual therapeutic agents of the combination concurrently but separately, or administration of the individual agents of the combination sequentially by any suitable route. The dosage of the individual therapeutic agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

Combinations as reported herein may include embodiments wherein one or more of Compound 1 and a CDK 4/6 inhibitor are administered as a pharmaceutically acceptable salt or as a free base. There is no requirement that both compounds be administered as the same pharmaceutically acceptable salt, but they may be. In particular embodiments combinations comprise a free base form of Compound 1 and a free base form of CDK 4/6 inhibitor. In other embodiments combinations comprise an HCl form of Compound 1 and an HCl form of a CDK 4/6 inhibitor. In some embodiments the CDK 4/6 inhibitor may be a free base. In some embodiments the CDK 4/6 inhibitor may be a pharmaceutically acceptable salt. In some embodiments the CDK 4/6 inhibitor may be a hydrate.

"Pharmaceutically acceptable salt" as used herein refers to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like.

Embodiments may be hydrochloride salts. Pharmaceutically acceptable salts may be derived from amino acids including, but not limited to, cysteine. Methods for producing compounds as salts are known to those of skill in the art (see, e.g., Stahl et al., Handbook of Pharmaceutical Salts: Properties, Selection, and Use, Wiley-VCH; Verlag Helvetica Chimica Acta, Zurich, 2002; Berge et al., J. Pharm. Sci. 66: 1, 1977).

An "effective amount" of a combination of therapeutic agents (e.g., Compound 1 and a CDK 4/6 inhibitor) is an amount sufficient to provide an observable therapeutic benefit compared to breast cancer left untreated in a subject or patient.

Active agents as reported herein can be combined with a pharmaceutically acceptable carrier to provide pharmaceutical formulations thereof. The particular choice of carrier and formulation will depend upon the particular route of administration for which the composition is intended.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, vaginal or implanted reservoir administration, etc. In some embodiments, the formulation comprises ingredients that are from natural or non-natural sources. In some embodiments, the formulation or carrier may be provided in a sterile form. Non-limiting examples of a sterile carrier include endotoxin-free water or pyrogen-free water.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids and their glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents that are commonly used in the manufacture of pharmaceutically acceptable solid, liquid, or other dosage forms may also be used for the purposes of formulation.

For oral administration, a compound or salt may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added. In addition preservatives may also be added. Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

"Immediate-release" is meant to include a conventional release, in which release of the drug starts immediately after administration. As used herein, the term "immediate release" includes dosage forms that allow the drug to dissolve in the gastrointestinal contents, with no intention of delaying or prolonging the dissolution or absorption of the drug. The objective is for the drug to be released rapidly after administration, for example for it to be possible to release at least 80% of the drug within approximately 30 minutes after commencement of dissolution in a dissolution test.

"Sustained-release" or "extended-release" includes dosage forms whose drug-release characteristics of time course and/or location are chosen to accomplish therapeutic or convenience objectives not offered by conventional dosage forms such as a solution or an immediate release dosage form.

The term "steady-state" means that a plasma level for a given active agent or combination of active agents, has been achieved and which is maintained with subsequent doses of the active agent(s) at a level which is at or above the minimum effective therapeutic level and is below the minimum toxic plasma level for a given active agent(s).

The term "single formulation" as used herein refers to a single carrier or vehicle formulated to deliver effective amounts of both therapeutic agents to a patient. The single vehicle is designed to deliver an effective amount of each of the agents along with any pharmaceutically acceptable carriers or excipients. In some embodiments, the vehicle is a tablet, capsule, pill, or a patch.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents (Compound 1 or a CDK 4/6 inhibitor) along with pharmaceutically acceptable carriers and excipients. In some embodiments, the unit dose is one or more tablets, capsules, pills, or patches administered to the patient at the same time. When agents are administered "simultaneously," they may be administered either as a single unit dose or as separate doses administered within close time proximity; in a non-limiting example, both agents may be separately administered within five minutes of each other.

The term "dose range" as used herein refers to an upper and a lower limit of an acceptable variation of the amount of agent specified. Typically, a dose of an agent in any amount within the specified range can be administered to patients undergoing treatment.

The term "treat" is used herein to mean to relieve, reduce or alleviate at least one symptom of a disease in a subject. For example, in relation to breast cancer, the term "treat" may mean to arrest, delay the onset (i.e., the period prior to clinical manifestation of a disease or symptom of a disease) and/or reduce the risk of developing or worsening a symptom of a disease. The term "protect" is used herein to mean prevent delay or treat, or all, as appropriate, development or continuance or aggravation of symptoms of the disease in a subject.

The term "subject" or "patient" is intended to include animals, which are capable of suffering from or afflicted with breast cancer. Examples of subjects or patients include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from breast cancer.

The term "about" or "approximately" usually means within 20%, more preferably within 10%, and most preferably still within 5% of a given value or range. Alternatively, especially in biological systems, the term "about" means approximately within a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein.

Exemplary cell proliferative disorders that may be treated using one or more compounds disclosed herein include, but are not limited to breast cancer, a precancer or precancerous condition of the breast, benign growths or lesions of the breast, and malignant growths or lesions of the breast, and metastatic lesions in tissue and organs in the body other than the breast. Cell proliferative disorders of the breast may include hyperplasia, metaplasia, and dysplasia of the breast.

A breast cancer that is to be treated may arise in a male or female subject. A breast cancer that is to be treated may arise in a premenopausal female subject or a postmenopausal female subject. A breast cancer that is to be treated may arise in a subject 30 years old or older, or a subject younger than 30 years old. A breast cancer that is to be treated has arisen in a subject 50 years old or older, or a subject younger than 50 years old. A breast cancer that is to be treated may arise in a subject 70 years old or older, or a subject younger than 70 years old.

A compound disclosed herein, or a pharmaceutically acceptable salt thereof, may be used to treat or prevent a cell proliferative disorder of the breast, or to treat or prevent breast cancer, in a subject having an increased risk of developing breast cancer relative to the population at large, or used to identify suitable candidates for such purposes. A subject with an increased risk of developing breast cancer relative to the population at large is a female subject with a family history or personal history of breast cancer. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old.

The term "enhanced effect" as used herein, refers to action of two agents that administered together provide a greater or improved result than when the individual agents are administered alone without co-administration of the other agent. Administration of the agents together may provide an enhanced effect when they are administered simultaneously or sequentially. Sequential administration of the agents includes administrations separated by several seconds, minutes, hours or days. Administration of the agents together may provide an enhanced effect when the agents are administered either as part of a single formulation, or when administered in separate formulations. Examples of agents that may be administered together include Compound 1 and CDK4/6 inhibtors. Additional examples of agents that may be administered together include i) Compound 1 and ribociclib; ii) Compound 1 and palbociclib; and iii) Compound 1 and abemaciclib.

The enhanced effect's greater or improved result may include, for example, one or more of the following: i) improved quality of tumor response, ii) improved speed of the tumor response, and iii) a tumor response that is more than additive of the response that might otherwise be achieved had the individual agents been administered alone. Examples of improved quality of tumor response may include complete regregression (CR) instead of partial regression (PR), stable disease (SD) or progressive disease (PD). Another example of improved quality of tumor response may include partial regression (PR) instead of stable disease (SD) or progressive disease (PD). Another example of improved quality of tumor response may include stable disease (SD) instead of progressive disease (PD). Controlled studies to determine whether administration of the agents together resulted with an enhanced effect of a tumor response more than additive of the corresponding responses achieved when the individual agents are respectively administered alone may be done, for example, in mice, rats, dogs, monkeys or other animals. Such controlled studies may evaluate, for example, the resulting tumor volume or metastatic or other status. Likewise, controlled studies may be used to determine an enhanced effect resulting in a faster tumor response.

Methods of Treatment

Provided herein is a combination therapy useful for the treatment of breast cancer. As discussed below, combinations provided herein may have a number of advantages.

One advantage of the combination disclosed herein is the unexpected enhanced effect of a combination of Compound 1 and a CDK 4/6 inhibitor on treatment of tumor grown inhibition and treatment of breast cancer.

In some embodiments, provided herein is a single pharmaceutical formulation containing a combination of Compound 1 and a CDK 4/6 inhibitor. An advantage provided herein is the enhanced effect that results in the treatment of breast cancer compared to treatment with a single dose of either drug. When the drugs are provided in a single unit dose or single formulation, the "pill burden" on a patient suffering from breast cancer is not increased.

As specified above, in one aspect, provided herein is a drug combination useful for treating, preventing, arresting, delaying the onset of and/or reducing the risk of developing, or reversing breast cancer in a mammal comprising administering to said mammal a combination therapy, comprising an effective amount of Compound 1 and an effective amount of a CDK 4/6 inhibitor.

In some embodiments, the subject to be treated (e.g., patient) is determined to be non-responsive or resistant to one or more breast cancer therapies, e.g., Compound 1. In other embodiments, the individual to be treated is responsive to Compound 1 therapy, but the therapy is improved with the administration of a CDK 4/6 inhibitor. For example, the patient is administered Compound 1 (e.g., 50 mg to 600 mg per day, 200 mg to 400 mg per day, or 300 mg per day for some period of time, e.g., more than one day, more than two days, more than three days, more than one week, for 21 days, more than one month, etc.). After that time, a CDK 4/6 inhibitor could be administered to that patient in combination with Compound 1.

Amounts of CDK 4/6 inhibitor may vary depending on the CDK 4/6 inhibitor that is used. For example, palbociclib may be administered, for example in a dosage of 75, 100, or 125 mg/day; ribociclib may be administered, for example, in a dosage of 200, 400, or 600 mg/day. Typically a dosage is administered orally as a single capsule for 21 consecutive days followed by a 7 day off-treatment period.

The daily dosage may be part of a cyclic regimen lasting 14 to 21 days or longer. The daily dosage amount may be administered as a single dosage or as multiple dosages.

One skilled in the art appreciates that the effective dose of the active drug may be lower than the actual amount administered. As such, provided herein are doses necessary to achieve a therapeutic dose.

In various embodiments, provided herein are methods of treating breast cancer by administering an effective amount of Compound 1 and a CDK 4/6 inhibitor, to an individual having breast cancer. The amount of the combination of agents is effective to treat the breast cancer. In one embodiment, the combination of agents has an enhanced effect. In one embodiment, even though one or more of the agents administered alone at a particular dosage may be effective, when administered in combination, at the same dosage of each agent, the treatment is more effective. For example, in one embodiment a combination of Compound 1 and palbociclib is more effective than is administration of either agent alone. In another embodiment a combination of Compound 1 and ribociclib is more effective than is administration of either agent alone.

Dosages

The optimal dose of the combination of agents for treatment of breast cancer can be determined empirically for each individual using known methods and will depend upon a variety of factors, including the activity of the agents; the age, body weight, general health, gender and diet of the individual; the time and route of administration; and other medications the individual is taking. Optimal dosages may be established using routine testing and procedures that are well known in the art.

For the combination therapy of the instant invention, the daily dose of Compound 1 is in the range of 50 mg-1000 mg. In some embodiments, the daily dose of Compound 1 is up to 1000 mg. In certain embodiments, the daily dose of Compound 1 is up to 500 mg. In various embodiments, the daily dose of Compound 1 is up to 300 mg. In certain embodiments, the daily dose of Compound 1 is 50 mg. In one embodiment, the daily dose is 300 mg.

For the combination therapy of the instant invention, the daily dose of Compound 2 is in the range of 50 mg-1000 mg. In some embodiments, the daily dose of Compound 2 is up to 1000 mg. In certain embodiments, the daily dose of Compound 2 is up to 500 mg. In various embodiments, the daily dose of Compound 2 is up to 300 mg. In certain embodiments, the daily dose of Compound 1 is 50 mg. In one embodiment, the daily dose is 300 mg.

For the combination therapy of the instant invention, the daily dose of Compound 3 is in the range of 50 mg-1000 mg. In some embodiments, the daily dose of Compound 3 is up to 1000 mg. In certain embodiments, the daily dose of Compound 3 is up to 500 mg. In various embodiments, the daily dose of Compound 3 is up to 300 mg. In certain embodiments, the daily dose of Compound 3 is 50 mg. In one embodiment, the daily dose is 300 mg.

The time of administration can be chosen such that both the drugs are administered simultaneously, separately or sequentially, either in the morning or at night. Alternatively, one drug can be administered in the morning and the other at night. In certain embodiments, both the drugs can be administered as a single tablet, capsule, pill, patch or jelly formulation, once daily, either in the morning or at night.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Pharmaceutical Formulations and Routes of Administration

Provided herein are pharmaceutical formulations comprising a combination of agents for the treatment of breast cancer. The pharmaceutical formulations may additionally comprise a carrier or excipient, stabilizer, flavoring agent, and/or coloring agent.

A combination of agents may be administered using a variety of routes of administration known to those skilled in the art. Routes of administration include oral administration. In certain embodiments, a pharmaceutical formulation comprising a combination of agents may be taken orally in the form of liquid, syrup, tablet, capsule, powder, sprinkle, chewtab, or dissolvable disk. Alternatively, pharmaceutical formulations of the present invention can be administered intravenously or transdermally. Additional routes of administration are known to those skilled in the art (see, e.g., Remington's Pharmaceutical Sciences, Gennaro A. R., Ed., 20th Edition, Mack Publishing Co., Easton, Pa.).

In some embodiments, the Compound 1 and CDK 4/6 inhibitor are formulated as a paste, jelly, or suspension. For example, the drugs are dissolved, entrapped or suspended in the form of drug particles, microencapsulated particles, or drug-polymer particles in a gelatinous solution or semisolid. An advantage of an oral jelly formulation is that it is easier to administer the drugs to patients who have difficulty swallowing tablets, capsules or pills. In certain embodiments, both agents are thoroughly mixed and suspended in an appropriate medium to form a paste or a gel. Additional agents can optionally be mixed to provide flavor during oral administration. Peanut butter or alginate, flavored with raspberry and a sweetener are examples of the many suitable taste masking agents. In various embodiments, the paste or jelly can also be formulated with suitable binders or excipients known in the art for topical administration.

Methods of preparing sustained release formulations in the form of tablets, capsules or pills are known in the art. In some embodiments, the sustained release formulation is prepared by coating the active ingredient of the drug with a polymer, preferably a water-insoluble polymer. For example, a water-insoluble polymer used in the pharmaceutical field as a sustained release coating agent, an enteric coating agent, or a gastric coating agent. The water-insoluble polymer can include, for example, ethyl cellulose, purified shellac, white shellac, aminoalkyl methacrylate copolymer RS, hydroxypropyl methylcellulose phthalate, hydroxypropyl methylcellulose acetate succinate, carboxymethylethylcellulose, cellulose acetate phthalate, methacrylic acid copolymer L, methacrylic acid copolymer LD, methacrylic acid copolymer S, aminoalkyl methacrylate copolymer E, or polyvinyl acetal diethylaminoacetate.

The type, degree of substitution and molecular weight of the water-insoluble polymers can depend on solubility of the active ingredient in water or an alcohol, the desired sustained release level and the like. The water-insoluble polymers can be used either alone or in combination. There can be further incorporated a hydrogenated oil, stearic acid, or cetanol as a coating auxiliary agent, and a middle-chain triglyceride, triacetin, triethyl citrate, or cetanol as a plasticizer.

In some embodiments, the sustained release formulation is a matrix-type tablet or granule. The active ingredient can be coated with up to 3 different types of polymers. These three different types of polymers can include: 1) a water insoluble polymer, such as ethylcellulose; 2) a pH independent gelling polymer, such as hydroxypropyl methylcellulose; and 3) a pH dependent gelling polymer, such as sodium alginate. These three different types of polymers can be used together to attenuate the release rate of the drugs.

Dosage Forms: Release Properties

Sustained-release formulations can achieve a degree of sustained effect. However, the exposure and/or the bioavailability of the active ingredient may vary based on a variety of factors, such as for example, the absorption window, the carriers or excipients used in the formulation, the mode of delivery of the formulation, and/or the transit time of the active ingredient through the gastrointestinal tract of the patient.

A combination therapy can contain at least one sustained-release portion for performing a sustained-release function and one immediate release portion for performing an immediate release function. In certain embodiments, when the combination therapy is in a single dosage form, it can be in the form of tablets formed from a mixture of sustained-release granules constituting a sustained-release portion and immediate-release granules constituting an immediate-release portion, a capsule preparation obtained by filling a capsule with sustained-release granules and immediate-release granules, or press-coated tablets in which an outer layer constituting an immediate-release portion is formed on an inner core constituting a sustained-release portion. There is, however, no limitation to the above embodiments.

Moreover, there are no particular limitations on the state of containment of each drug in the composition or in an immediate-release portion or a sustained-release portion; the Compound 1 may be dispersed uniformly in the composition, immediate release portion or sustained release portion, or may be contained in only one part of the composition, immediate-release portion or sustained-release portion, or may be contained such that there is a concentration gradient.

A sustained-release portion in the composition according to the present invention can contain at least one non-pH-dependent polymeric substance or pH-dependent polymeric substance for controlling drug release.

A non-pH-dependent polymeric substance used herein can comprise a polymeric substance whose charge state hardly changes under pH conditions generally found in the gastrointestinal tract, specifically from pH 1 to pH 8. This means, for example, a polymeric substance that does not have functional groups whose charge state changes depending on the pH such as basic functional groups such as amino groups or acidic functional groups such as carboxylic acid groups. Note that the non-pH-dependent polymeric substance can be included for giving the composition according to the present invention a sustained-release function, but may also be included for another purpose. Moreover, the non-pH-dependent polymeric substance used in the present invention may be water-insoluble, or may swell in water or dissolve in water to form a gel.

Examples of water-insoluble non-pH-dependent polymeric substances include, but are not limited to, cellulose ethers, cellulose esters, and methacrylic acid-acrylic acid copolymers (trade name Eudragit, manufactured by Rohm GmbH & Co. KG, Darmstadt, Germany). Examples include, but are not limited to, cellulose alkyl ethers such as ethylcellulose (trade name Ethocel, manufactured by Dow Chemical Company, USA), ethyl methylcellulose, ethyl propylcellulose or isopropylcellulose, and butylcellulose, cellulose aralkyl ethers such as benzyl cellulose, cellulose cyanoalkyl ethers such as cyanoethylcellulose, cellulose organic acid esters such as cellulose acetate butyrate, cellulose acetate, cellulose propionate or cellulose butyrate, and cellulose acetate propionate, ethyl acrylate-methyl methacrylate copolymers (trade name Eudragit NE, manufactured by Rohm GmbH & Co. KG, Darmstadt, Germany), and aminoalkyl methacrylate copolymer RS (trade names Eudragit RL, Eudragit RS). There are no particular limitations on the mean particle diameter of a water-insoluble polymer used in the present invention, but usually the lower this mean particle diameter the better the performance, with the mean particle diameter preferably being from 0.1 to 100 μm, more preferably from 1 to 50 μm, particularly preferably from 3 to 15 μm, most preferably from 5 to 15 μm. Moreover, examples of water-soluble or water-swelling non-pH-dependent polymeric substances include, but are not limited to, polyethylene oxide (trade name Polyox, manufactured by Dow Chemical Company, molecular weight 100,000 to 7,000,000), low-substituted hydroxypropyl cellulose (trade name L-HPC, manufactured by Shin-Etsu Chemical, Japan), hydroxypropyl cellulose (trade name HPC, manufactured by Nippon Soda, Co., Ltd, Japan), hydroxypropyl methylcellulose (trade names Metolose 60SH, 65SH, 90SH, manufactured by Shin-Etsu Chemical, Japan), and methylcellulose (trade name Metolose SM, manufactured by Shin-Etsu Chemical, Japan).

In some embodiments a single non-pH-dependent polymeric substance may be contained in the composition, or a plurality of the non-pH-dependent polymeric substances may be contained. The non-pH-dependent polymeric substance, if used in embodiments reported herein, may be a water-insoluble polymeric substance, more preferably ethylcellulose, an ethyl acrylate-methyl methacrylate copolymer (trade name Eudragit NE), or an aminoalkyl methacrylate copolymer RS (trade name Eudragit RL, Eudragit RS). Particularly preferable is at least one of ethylcellulose and an aminoalkyl methacrylate copolymer RS. Most preferable is ethylcellulose. There are no particular limitations on the amount of the non-pH-dependent polymeric substance contained in the composition; this amount can be adjusted as appropriate in accordance with the purpose such as controlling sustained drug release.

A pH-dependent polymeric substance that can be used in embodiments reported herein may be a polymeric substance whose charge state changes under pH conditions generally found in the gastrointestinal tract, specifically from pH 1 to pH 8. This means, for example, a polymeric substance having functional groups whose charge state changes depending on the pH such as basic functional groups such as amino groups or acidic functional groups such as carboxylic acid groups. The pH-dependent functional groups of the pH-dependent polymeric substance are preferably acidic functional groups, with the pH-dependent polymeric substance most preferably having carboxylic acid groups.

A pH-dependent polymeric substance used in the present invention may be water-insoluble, or may swell in water or dissolve in water to form a gel. Examples of pH-dependent polymeric substances used in the present invention include, but are not limited to, enteric polymeric substances. Examples of enteric polymeric substances include, but are not limited to, methacrylic acid-methyl methacrylate copolymers (Eudragit L100, Eudragit S100, manufactured by Rohm GmbH & Co. KG, Darmstadt, Germany), methacrylic acid-ethyl acrylate copolymers (Eudragit L100-55, Eudragit L30D-55, manufactured by Rohm GmbH & Co. KG, Darmstadt, Germany), hydroxypropyl methylcellulose phthalate (HP-55, HP-50, manufactured by Shin-Etsu Chemical, Japan), hydroxypropyl methylcellulose acetate succinate (AQOAT, manufactured by Shin-Etsu Chemical, Japan), carboxymethyl ethylcellulose (CMEC, manufactured by Freund Corporation, Japan), and cellulose acetate phthalate.

Examples of pH-dependent polymeric substances that swell in water or dissolve in water to form a gel include, but are not limited to, alginic acid, pectin, carboxyvinyl polymer, and carboxymethyl cellulose. In the present invention, a single pH-dependent polymeric substance may be contained in the composition, or a plurality of pH-dependent polymeric substances may be contained. The pH-dependent polymeric substance used in the present invention is preferably an enteric polymeric substance, more preferably a methacrylic acid-ethyl acrylate copolymer, a methacrylic acid-methyl methacrylate copolymer, hydroxypropyl methylcellulose phthalate, or hydroxypropyl methylcellulose acetate succinate, particularly preferably a methacrylic acid-ethyl acrylate copolymer.

When using a pH-dependent polymeric substance in the manufacturing process of a composition according to the present invention, a commercially available product of a powder type or a granular type, or a suspension type in which the pH-dependent polymeric substance has been dispersed in a solvent in advance can be used as is, or such a commercially available product can be used dispersed in water or an organic solvent. The lower the particle diameter of the pH-dependent polymeric substance the better the performance, with the pH-dependent polymeric substance preferably being of the powder type. In the case of a methacrylic acid-ethyl acrylate copolymer, an example is Eudragit L100-55. There are no particular limitations on the mean particle diameter of a pH-dependent polymeric substance used in the present invention, but the mean particle diameter is preferably from 0.05 to 100 μm, more preferably from 0.05 to 70 μm, most preferably from 0.05 to 50 μm. Moreover, there are no particular limitations on the amount of the pH-dependent polymeric substance, for example, in the case of an enteric polymeric substance, the amount is generally from 0.1 to 90 parts by weight, preferably from 1 to 70 parts by weight, more preferably from 5 to 60 parts by weight, particularly preferably from 10 to 50 parts by weight, based on 100 parts by weight of the composition.

A combination therapy according to embodiments reported herein may further contain any of various additives, such as any of various pharmacologically acceptable carriers such as diluents, lubricants, binders and disintegrants, as well as preservatives, colorants, sweeteners, plasticizers, film coating agents and so on, as necessary. Examples of diluents include, but are not limited to, lactose, mannitol, dibasic calcium phosphate, starch, pregelatinized starch, crystalline cellulose, light silicic anhydride, synthetic aluminum silicate, magnesium aluminate metasilicate or the like. Examples of lubricants include, but are not limited to, magnesium stearate, calcium stearate, talc, sodium stearyl fumarate or the like. Examples of binders include, but are not limited to, hydroxypropyl cellulose, methylcellulose, sodium carboxymethyl cellulose, hydroxypropyl methylcellulose, polyvinylpyrrolidone or the like. Examples of disintegrants include, but are not limited to, carboxymethyl cellulose, calcium carboxymethyl cellulose, croscarmellose sodium, sodium carboxymethyl starch, low-substituted hydroxypropyl cellulose or the like. Examples of preservatives include, but are not limited to, paraoxybenzoic acid esters, chlorobutanol, benzyl alcohol, phenethyl alcohol, dehydroacetic acid, sorbic acid or the like. Preferable examples of colorants include, but are not limited to, water-insoluble lake pigments, natural pigments (e.g., beta-carotene, chlorophyll, red ferric oxide), yellow ferric oxide, red ferric oxide, black ferric oxide or the like. Preferable examples of sweeteners include, but are not limited to, sodium saccharin, dipotassium glycyrrhizate, aspartame, stevia or the like. Examples of plasticizers include, but are not limited to, glycerol fatty acid esters, triethyl citrate, propylene glycol, polyethylene glycol or the like. Examples of film coating agents include, but are not limited to, hydroxypropyl methylcellulose, hydroxypropyl cellulose or the like.

Manufacturing Methods

To manufacture embodiments as reported herein, a single conventional method, or a combination of conventional methods, can be used. For example, when manufacturing drug-containing granules as a sustained-release portion or an immediate-release portion, granulation is the main operation, but this may be combined with other operations such as mixing, drying, sieving, and classification. As the granulation method, for example, a wet granulation method in which a binder and a solvent are added to the powder and granulation is carried out, a dry granulation method in which the powder is compressed and granulation is carried out, a molten granulation method in which a binder that melts on heating is added and heating and granulation are carried out, or the like can be used.

Furthermore, in accordance with the granulation method, an operating method such as a mixing granulation method using a planetary mixer, a screw mixer or the like, a high-speed mixing granulation method using a Henschel mixer, a Super mixer or the like, an extruding granulation method using a cylindrical granulator, a rotary granulator, a screw extruding granulator, a pellet mill type granulator or the like, a wet high-shear granulation method, a fluidized-bed granulation method, a compression granulation method, a crushing granulation method, or a spraying granulation method can be used. After the granulation, drying using a dryer, a fluidized bed or the like, cracking, and sieving can be carried out to obtain the granules or fine granules for use. Moreover, a granulation solvent may be used when preparing the composition according to the present invention. There are no particular limitations on such a granulation solvent, which may be water or any of various organic solvents, for example, water, a lower alcohol such as methanol or ethanol, a ketone such as acetone or methyl ethyl ketone, methylene chloride, or a mixture thereof.

For sustained-release granules contained in embodiments, at least one drug and at least one selected from non-pH-dependent polymeric substances and pH-dependent polymeric substances are mixed together, a diluent and a binder are added as necessary, and granulation is carried out to obtain granular matter. The granular matter obtained is dried using a tray dryer, a fluidized bed dryer or the like, and sieving is carried out using a mill or an oscillator, whereby the sustained-release granules can be obtained. Alternatively, as a method of manufacturing sustained-release granules in the present invention, it is possible to add at least one drug, at least one selected from non-pH-dependent polymeric substances and pH-dependent polymeric substances, and as necessary a diluent and a binder using a dry compactor such as a roller compactor or a slug tabletting machine, and carry out compression-molding while mixing, and then carry out granulation by cracking down to a suitable size. The granular matter prepared using such a granulator may be used as is as granules or fine granules according to the present invention, or may be further cracked using a power mill, a roll granulator, a rotor speed mill or the like, and sieved to obtain sustained-release granules. Note that immediate-release granules can also be manufactured as for the sustained-release granules.

A compression-molded product can be manufactured as a drug-containing sustained-release portion or immediate-release portion, or as a composition reported herein using a single conventional method, or a combination of conventional methods. For example, at least one drug, at least one selected from non-pH-dependent polymeric substances and pH-dependent polymeric substances, a diluent such as mannitol or lactose, a binder such as polyvinylpyrrolidone or crystalline cellulose, a disintegrant such as carmellose sodium or crospovidone, and a lubricant such as magnesium stearate or talc are used, and tableting is carried out using an ordinary method, whereby the compression-molded product can be obtained. In this case, tabletting is the main operation in the method of manufacturing the compression-molded product, but this may be combined with other operations such as mixing, drying, sugar coating formation, and coating.

Examples of the method for the tabletting include, but are not limited to, direct compression molding in which at least one drug and pharmacologically acceptable additives are mixed together and then the mixture is directly compression-molded into tablets using a tabletting machine, and dry granule compression or wet granule compression in which sustained-release granules or immediate-release granules according to the present invention are subjected to compression-molding after adding a lubricant or a disintegrant as necessary. There are no particular limitations on the tabletting machine used in the compression molding, for example, a single-punch tabletting machine, a rotary tabletting machine, or a press-coated tabletting machine can be used.

Drug-containing sustained-release granules or immediate-release granules, or compression-molded product according to embodiments herein can be used as is in the form of granules or a tablet as the composition, but may also be subjected to further processing to manufacture the composition. For example, the compression-molded product or granules can be given a film coating using a film base material such as ethylcellulose, casein, methylcellulose, hydroxypropyl methylcellulose, methacrylic acid copolymer L, cellulose acetate phthalate, shellac or the like, or given a sugar coating using a sugar coating liquid containing saccharose, sugar alcohol, gum arabic powder, talc or the like, thus producing film-coated tablets or sugar-coated tablets. One solvent in this coating technique may be purified water, but an organic solvent such as an alcohol, a ketone, an ether or a chlorinated hydrocarbon, or a mixture thereof can also be used. For example, ethanol, acetone, methylene chloride or the like can be used as an organic solvent. Moreover, as the coating apparatus, an apparatus ordinarily used in coating techniques for manufacturing medicines can be used, with examples including a spray coating apparatus in which the coating is carried out by spraying a coating liquid or the like, and a rotor fluidized bed granulator for layering.

In the case of manufacturing capsule preparations, capsule preparations can be manufactured by filling sustained-release granules or immediate-release granules as above, or mini-tablets into hard gelatin capsules or HPMC capsules using an automatic capsule filling machine. Alternatively, in the case of the preparations for per-tube administration or a dry syrup that is used mixed with water or the like when taken, sustained-release granules or immediate-release granules as above can be mixed with a thickener or a dispersant so as to disperse these granules, the mixture then being made into granules or tablets. Furthermore, a liquid or jelly can be made using water, and substances selected from dispersants, emulsifiers, thickeners, preservatives, pH adjustors, sweeteners, flavorings, fragrances and so on. However, with respect to other manufacturing methods, there are no limitations to the above.

So that embodiments described herein may be more fully understood, the following examples are set forth. It should be understood that these examples are for illustrative purposes only and are not to be construed as limiting.

EXAMPLES

In aggregate, the data below demonstrate combinations with palbociclib, a CDK4/6 inhibitor can significantly enhance the antiproliferative and antitumor effects of Compounds 1, 2 and 3 in cell lines harboring $ER\alpha^{WT}$ and/or $ER\alpha^{Y537S}$ and for Compound 1 in a patient-derived xenograft model representing $ER\alpha^{WT/Y537S}$ breast cancer.

Materials and Methods

Cell Lines Tested

MCF7 BUS cells (Coser, el al., (2003) *PNAS* 100(24): 13994-13999) were maintained in Dulbecco's Modified Eagle Medium supplemented with 10% FBS, 4 mM L-glutamine and 1× non-essential amino acids. Lenti-X 293T cells (Clontech, Cat #632180) were routinely cultured in Dulbecco's Modified Eagle Medium supplemented with 10% FBS. MCF7 lines engineered to overexpress $ER\alpha^{WT}$ (MCF7.6) or $ER\alpha^{Y537S}$ (MCF7.7) were derived from the MCF7 BUS cells at H3 Biomedicine, Inc. The ST941 cell line was derived from a patient-derived breast cancer xenograft (PDX) model (ST941) positive for the endogenous Y537S hotspot mutation in ERα. HEK293T cells used for virus production were sourced from Clontech. All cell lines were verified free of *Mycobacterium* contamination and their identity confirmed by short tandem repeat analysis of 9 markers.

Cell Line Maintenance and Study Conditions

Medium conditions for growth of engineered MCF7 lines included Dulbecco's Modified Eagle's medium (DMEM) (ATCC® 30-2002™) supplemented with 10% v/v Fetal Bovine Serum (ATCC® 30-2021™), 2.0 mM L-glutamine (ATCC® 30-2214™), 1.0% non-essential amino acids (ThermoFisher #11140050), and 5 μg/mL Blastidicin (ThermoFisher #A1113903). Medium conditions for growth of ST941 cells included Dulbecco's Modified Eagle's medium (DMEM) (ATCC® 30-2002™) supplemented with 20% v/v Fetal Bovine Serum (ATCC® 30-2021™). All cells were maintained prior to and during experiments at 37° C., 5% $CO_2$, and at 95% relative humidity. Cells were passaged 2 to 3 times per week and passage number was limited to between 6 and 20. During in vitro experiments cells were seeded at appropriate densities to provide logarithmic growth during and at least 24 hours beyond the experiment target compound exposure duration.

Site-Direct Mutagenesis and Cell Line Engineering

The QuikChange II XL Site-Directed Mutagenesis Kit (Agilent Technologies, Cat #200523) was used to generate the Y537S mutation within the ERα exon 8. Wild-type ESR1 cDNA (GeneCopoeia Inc., Cat #GC-A0322, accession no. NM 000125) was used as a template with the following mutagenesis primers (where the underlined nucleotides represent site mutations): Y537S: F-AAG AAC GTG GTG CCC CTC T̲C̲T GAC CTG CTG CTG GAG ATG (SEQ ID NO: 1), R-CAT CTC CAG CAG CAG GTC A̲G̲A GAG GGG CAC CAC GTT CTT (SEQ ID NO: 2). WT and mutantESRI cDNAs were cloned into the designation lentiviral vector pLenti6.3N5-Dest (Invitrogen, Cat #V533-06). To make lentiviral particles, DNAs (WT and mutant ESR1) were co-transfected with packaging plasmids into HEK293T cells using lipofectamine 2000. 48 h post-transfection, virus containing media was filtered and added to MCF7 cells in the presence of 8 μM polybrene overnight. The following day cells were placed under selection with 6 μM blasticidin for 2 weeks for stable expression.

Compound Preparation and Presentation to Cells

These preparatory methods relate to Examples 1-3, below. Compounds for assay were prepared as stocks in 90% dimethyl sulfoxide (DMSO), assessed for purity by LC/MS, and serially diluted in DMSO using a low-volume liquid handler (VIAFLO ASSIST and VIAFLO 11 electronic 16-channel pipette, 0.5-12.5 µL) in an 11-point half-log serial dilution to create a master dose response (MDR) source used for all tests.

Transfer of compounds from the MDR source plate to cell plates were accomplished directly by low-energy acoustic transfer (ATS100, EDC Biosystems) using custom combination-specific transfer maps (Transfer Track, BioSero). After transfer of compounds to the assay plate, the dose-response range experienced by cells was typically 2.5 µM-25 µM (5 logs), and final DMSO concentration in the assay was 0.1%, uniformly. Each assay plate was self-anchored containing duplicate dilution series of each compound as a single-agent, duplicate 11×11 combination matrices, vehicle/DMSO negative controls, cidal positive controls (0.5 µM bortezomib+0.5 µM staurosporine), and the static control agent cycloheximide (3 µM).

Measurement of Anti-Proliferative Activity of Treated Cells

Cell proliferation and viability assays were performed 144 hours post-treatment using CellTiter-Glo® Luminescent Cell Viability Assay reagent (Promega) according to the manufacturer's instructions (CellTiter-Glo® Luminescent Cell Viability Assay Technical Bulletin Instructions for Use of Product(s) G7570, G7571, G7572, G7573 Literature #TB288, Revised 3/15), and then measuring the luminescent signal on a microtiter plate reader (Envision, PE).

Cell proliferation was evaluated using the time zero (TO) signal as the positive control and the within-plate vehicle wells (DMSO) as the negative control. Data was converted to percent inhibition and falls into the range from 0% to 100% of growth where 0% equals the signal at TO and 100% equals uninhibited or maximal growth. Cell growth at or near 0% is considered a static response.

Cell viability was evaluated using the response data for within-plate cidal control compounds (0.5 µM bortezomib/0.5 µM staurosporine) and the TO signal as the negative control. Data was converted to percent inhibition and falls into the range from −100% to 0%. Cell growth at or near −100% is considered a cidal response.

Determination of Compound Synergy In Vitro

Compounds 1, 2, and 3 and the CDK4/6 inhibitor palbociclib were tested as single-agents and in combinations against the MCF7.6, MCF7.7 and ST941 breast cancer cell line models. Relative percent inhibition data were calculated by in-house data analysis software (ECABIA, H3 Biomedicine) as described, and then transformed into Chalice software (Horizon Discovery) format compatible with further analysis (i.e. −100%, 0%, and 100% were converted to 200% (cidal), 100% (static), and 0% (no effect), respectively.)

Combination effects were then assessed using Chalice software comparing combination responses to their matched single-agent effects using the Loewe Additivity Model (Lehar J et al 2009 and Zimmermann G R et al 2006). Drug concentration ranges where synergistic effects occurred can be visualized in Chalice by comparing the full Dose-matrix Chart to the Loewe Additivity Model Chart, and by direct observation of the Excess Response Chart. Quantitative assessment can be made within a study or across anchored studies performed similarly by the area and intensity of the combination response which is provided by the Chalice synergy score. Self-cross experiments and tests with other additive-only combinations served as baseline controls.

Xenograft Generation, Dosing and Measurement of Antitumor Activity

To generate patient derived xenografts (PDX) representing $ER\alpha^{WT/Y537S}$ breast cancer, solid tumor tissues from the ST941 xenograft model (ST941) bearing the $ER\alpha^{WT/Y537S}$ were cut into 70 mg pieces, mixed with Matrigel (Corning, 354234) and subcutaneously implanted into the right flank of female athymic Nude (Crl:NU(NCr)-Foxn1nu) mice supplied with drinking water containing estradiol (Sigma-Aldrich, E1024-25G). When the tumor volumes (TV) reached between 125-250 mm³, 72 animals were selected based on TV and randomized into nine treatment groups of 8 animals per group Beginning three days prior to treatment and for the remainder of the study, exogenous estradiol was no longer supplied in the drinking water. Per os (PO) treatment with Compound 1 (3 and 10 mg/kg) and palbociclib (25 and 75 mg/kg) or vehicle was administered once daily (QD). The PO administration volume (0.1 mL/10 g body weight) was calculated from the body weight (BW) prior to compound administration. Body weights and tumor volume measurements were recorded twice per week.

The TV in mm³ was calculated according to the following formula:

$$TV = length \times width^2 \times 0.5$$

length: largest diameter of tumor (mm)
width: diameter perpendicular to length (mm)
The Tumor Growth Inhibition % (TGI) was calculated according to the following formula:

$$\text{Tumor Growth Inhibition \% } (TGI) = \frac{\text{Average Control } TV \text{ Day } X - \text{Treatment } TV \text{ Day } X}{Average Control \ TV \text{ Day } X} \times 100$$

where Day X is any day of measurement.

The antitumor effects of the treatment, stable (SD) and progressive (PD) disease were defined by the Xenograft Model Response Criteria (see below). Mice with >20% body weight loss compared with Day 0 body weight, or bearing tumor with a mass >10% animal body weight were euthanized to prevent any pain and suffering to the animal. All studies were performed under guidelines set forth by the START IACUC and defined in the START Animal Care and Use Program (Protocol 09-001).

Statistical Analysis

Data are expressed as mean SEM for TV and BW. The differences in tumor volume on Day 38 between the vehicle and Compound 1 or palbociclib treated groups were analyzed by two way ANOVA followed by Tukey's test. The relative body weight changes were analyzed by two way ANOVA followed by Tukey's test. Statistical analyses were performed using GraphPad Prism version 7.0 (GraphPad Software, La Jolla, Calif.).

Xenograft Model Response Criteria

Progressive disease (PD): 3 consecutive measurements >120% of starting volume or 3 consecutive increasing measurements from best response, Stable disease (SD): 3 consecutive measurements >50% and <120% of starting volume.

Formulation of Compound 1 and Palbociclib for In Vivo Xenograft Study

In the in vivo xenograft Examples 4, reported below, Compound 1 and palbociclib were formulated as follows.

This type of formulation is exemplary and not required in particular embodiments of the invention. In these examples palbociclib was presented as a free base. Compound 1 was formulated in 10% 2-Hydroxypropyl-β-CycloDextrin (HPβCD) in 5% Dextrose, vortexed and sonicated until clear.

Palbociclib was formulated in 50 mM Sodium Lactate at pH 4.0. The compound was stable for 7 days in this formulation.

Example 1—Compound 1 and Palbociclib

In Examples 1-4, Compound 1 was present as an HCl salt.

Figure 2:
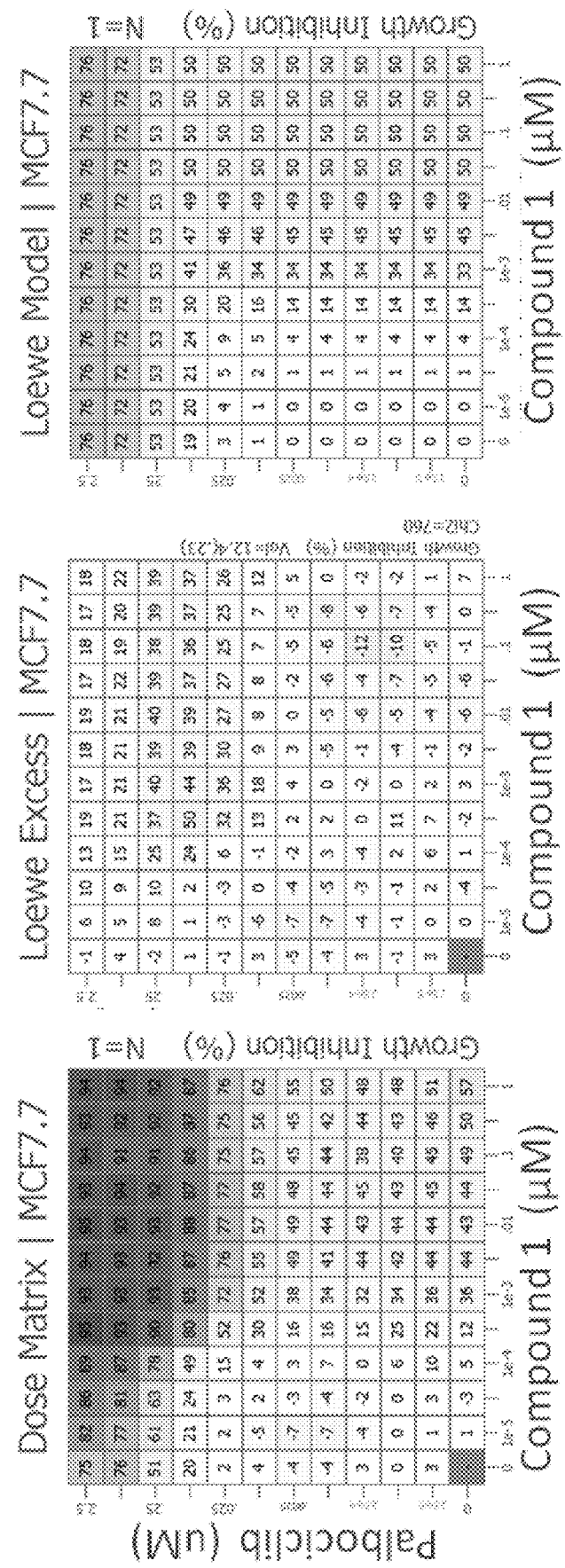
FIG. 2 shows viability of MCF7.7 cells treated for 144 hours with different doses of Compound 1 and palbociclib. Compound 1 and palbociclib synergistically inhibit growth of MCF7.7 cells in vitro. Inhibition of cell viability was measured using CellTiter-Glo, and Chalice software was used to calculate excess inhibition over Loewe additivity for each Compound 1 and palbociclib dose combination.
Figure 3:
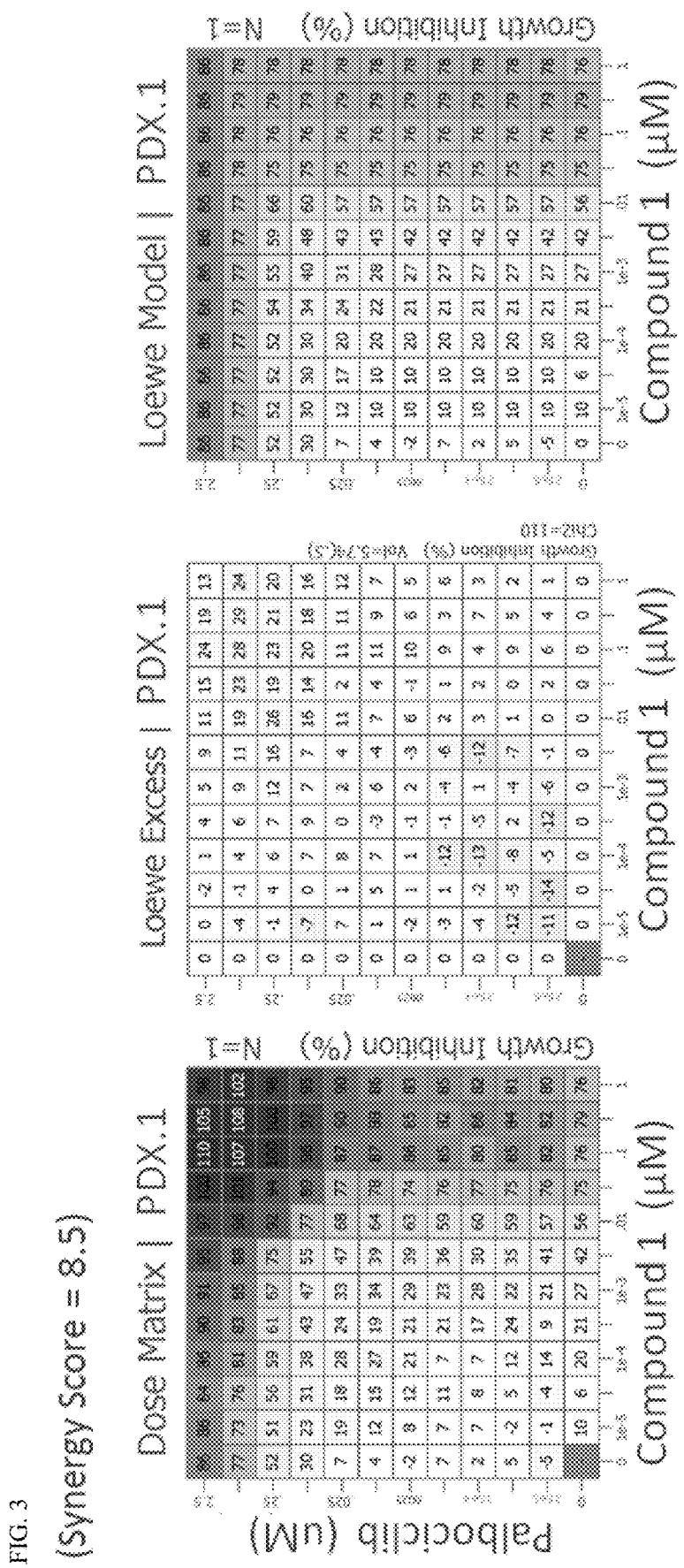
FIG. 3 shows ST941 cells treated for 144 hours with different doses of Compound 1 and palbociclib. Compound 1 and palbociclib synergistically inhibit growth of ST941 cells in vitro. Inhibition of cell viability was measured using CellTiter-Glo, and Chalice software was used to calculate excess inhibition over Loewe additivity for each Compound 1 and palbociclib dose combination.

FIGS. 1, 2, and 3 show that Compound 1 and palbociclib synergistically inhibit growth of breast cancer cell models in vitro. MCF7.6 cells were treated for 144 hours with different doses of Compound 1 and palbociclib and appear in FIG. 1. MCF7.7 cells were treated for 144 hours with different doses of Compound 1 and palbociclib and appear in FIG. 2. ST941 cells were treated for 144 hours with different doses of Compound 1 and palbociclib and appear in FIG. 3. Inhibition of cell viability was measured using CellTiter-Glo, and Chalice software was used to calculate excess inhibition over Loewe additivity for each Compound 1 and palbociclib dose combination. As single agents, the highest doses of 1.0 μM Compound 1 and 2.5 μM palbociclib did not fully result in cell stasis, but for all cell models tested the combination of 1.0 μM Compound 1 and 2.5 μM palbociclib led to complete cell stasis (i.e. 100% effect). In addition, over a range of lower doses Compound 1 and palbociclib when combined, reduced cell proliferation to a greater extent compared to the corresponding single-agent doses. Excess inhibition over additivity was calculated using the Loewe Additivity Model and synergistic values were observed starting from 0.010 μM Compound 1 and 0.025 μM palbociclib.

Example 2—Compound 2 and Palbociclib

Figure 4:
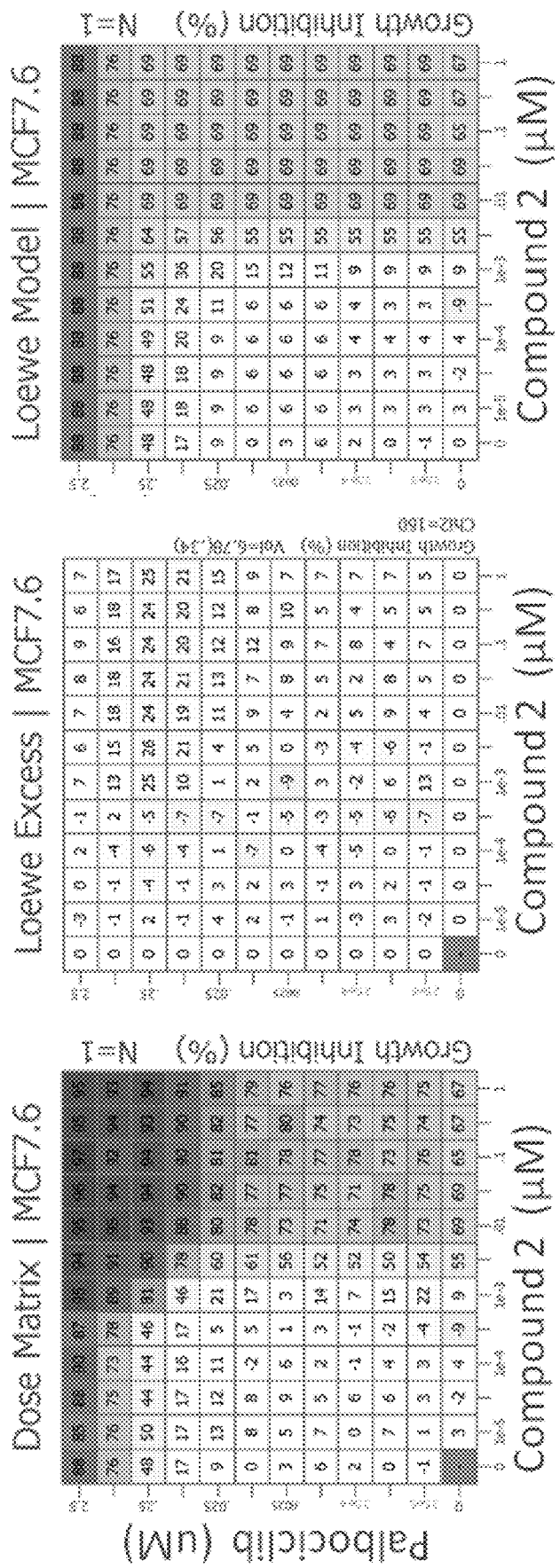
FIG. 4 shows M CF7.6 cells treated for 144 hours with different doses of Compound 2 and palbociclib. Compound 2 and palbociclib synergistically inhibit growth of MCF7.6 cells in vitro. Inhibition of cell viability was measured using CellTiter-Glo, and Chalice software was used to calculate excess inhibition over Loewe additivity for each Compound 2 and palbociclib dose combination.
Figure 5:
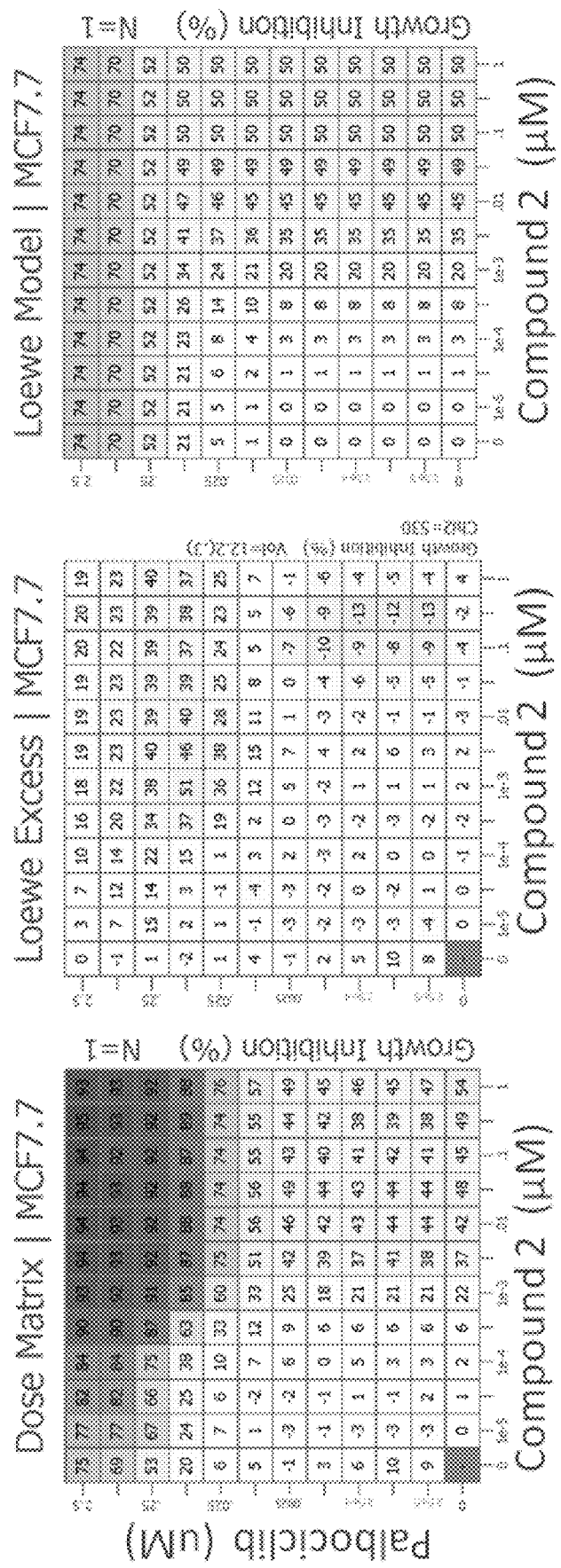
FIG. 5 shows MCF7.7 cells treated for 144 hours with different doses of Compound 2 and palbociclib. Compound 2 and palbociclib synergistically inhibit growth of MCF7.7 cells in vitro. Inhibition of cell viability was measured using CellTiter-Glo, and Chalice software was used to calculate excess inhibition over Loewe additivity for each Compound 2 and palbociclib dose combination.
Figure 6:
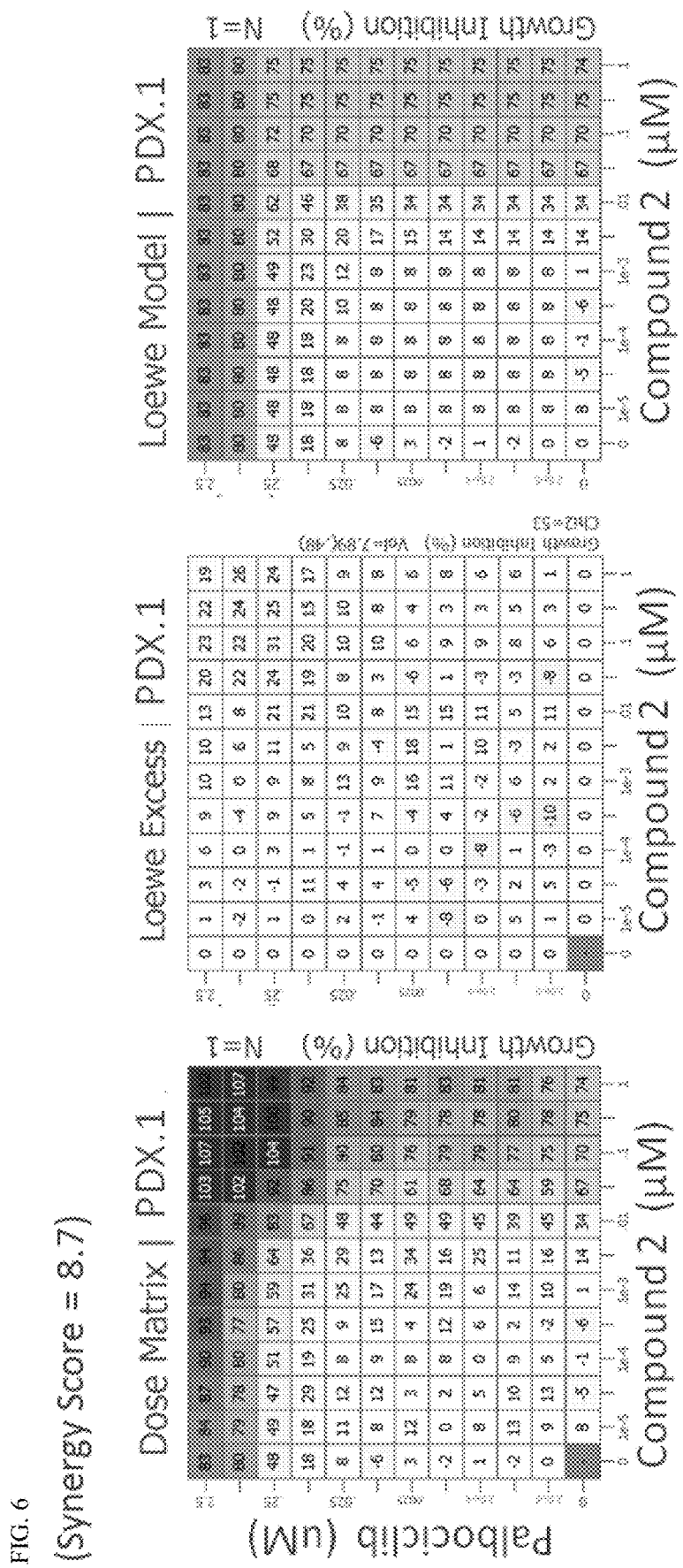
FIG. 6 shows ST941 cells treated for 144 hours with different doses of Compound 2 and palbociclib. Compound 2 and palbociclib synergistically inhibit growth of ST941 cells in vitro. Inhibition of cell viability was measured using CellTiter-Glo, and Chalice software was used to calculate excess inhibition over Loewe additivity for each Compound 2 and palbociclib dose combination.

FIGS. 4, 5, and 6 show that Compound 2 and palbociclib synergistically inhibit growth of breast cancer cell models in vitro. MCF7.6 cells were treated for 144 hours with different doses of Compound 2 and palbociclib and appear in FIG. 4. MCF7.7 cells were treated for 144 hours with different doses of Compound 2 and palbociclib and appear in FIG. 5. ST941 cells were treated for 144 hours with different doses of Compound 2 and palbociclib and appear in FIG. 6. Inhibition of cell viability was measured using CellTiter-Glo, and Chalice software was used to calculate excess inhibition over Loewe additivity for each Compound 2 and palbociclib dose combination. As single agents, the highest doses of 1.0 μM Compound 2 and 2.5 μM palbociclib did not fully result in cell stasis, but for all cell models tested the combination of 1.0 μM Compound 2 and 2.5 μM palbociclib led to complete cell stasis (i.e. 100% effect). In addition, over a range of lower doses Compound 2 and palbociclib when combined, reduced cell proliferation to a greater extent compared to the corresponding single-agent doses. Excess inhibition over additivity was calculated using the Loewe Additivity Model and synergistic values were observed starting from 0.010 μM Compound 2 and 0.025 μM palbociclib.

Example 3—Compound 3 and Palbociclib

Figure 7:
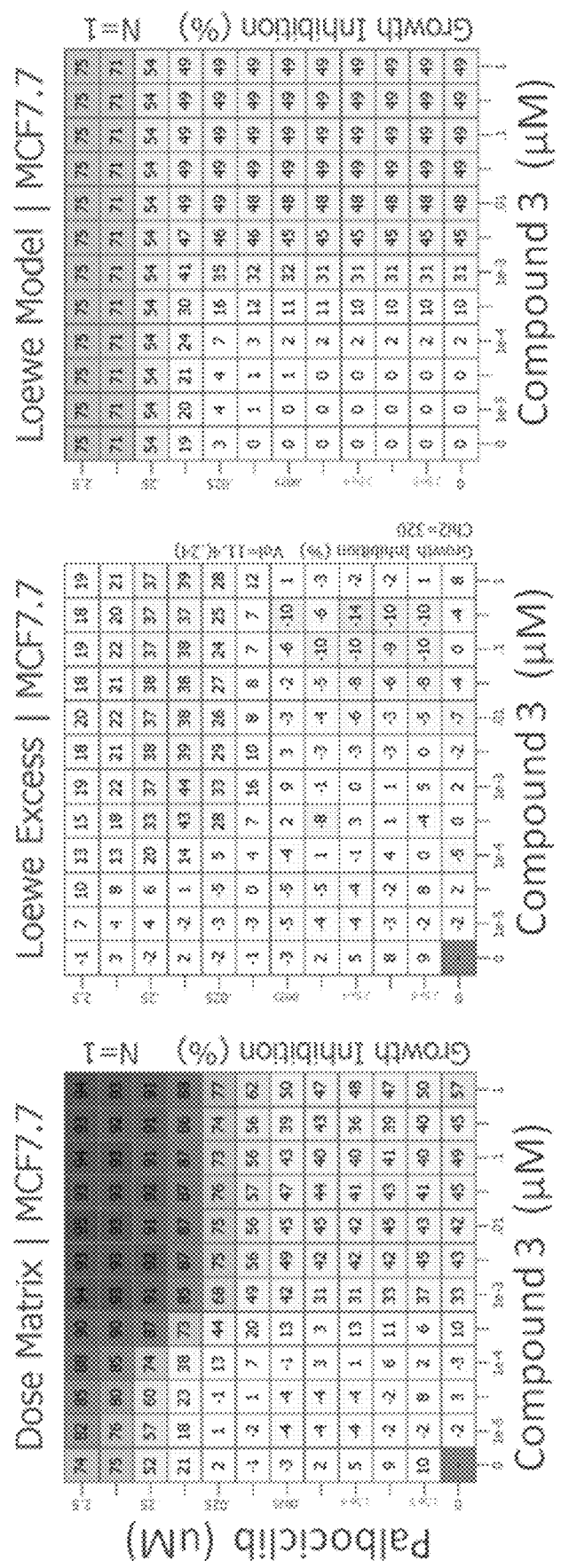
FIG. 7 shows MCF7.7 cells treated for 144 hours with different doses of Compound 3 and palbociclib. Compound 3 and palbociclib synergistically inhibit growth of MCF7.7 cells in vitro. Inhibition of cell viability was measured using CellTiter-Glo, and Chalice software was used to calculate excess inhibition over Loewe additivity for each Compound 3 and palbociclib dose combination.

FIG. 7 shows that Compound 3 and palbociclib synergistically inhibit growth of MCF7.7 breast cancer cell model in vitro. MCF7.7 cells were treated for 144 hours with different doses of Compound 3 and palbociclib. Inhibition of cell viability was measured using CellTiter-Glo, and Chalice software was used to calculate excess inhibition over Loewe additivity for each Compound 3 and palbociclib dose combination. As single agents, the highest doses of 1.0 μM Compound 3 and 2.5 μM palbociclib did not fully result in cell stasis, but the combination of 1.0 μM Compound 3 and 2.5 μM palbociclib led to complete cell stasis (i.e. 100% effect). In addition, over a range of lower doses Compound 3 and palbociclib when combined, reduced cell proliferation to a greater extent compared to the corresponding single-agent doses. Excess inhibition over additivity was calculated using the Loewe Additivity Model and synergistic values were observed starting from 0.010 μM Compound 3 and 0.025 μM palbociclib.

Figure 8:
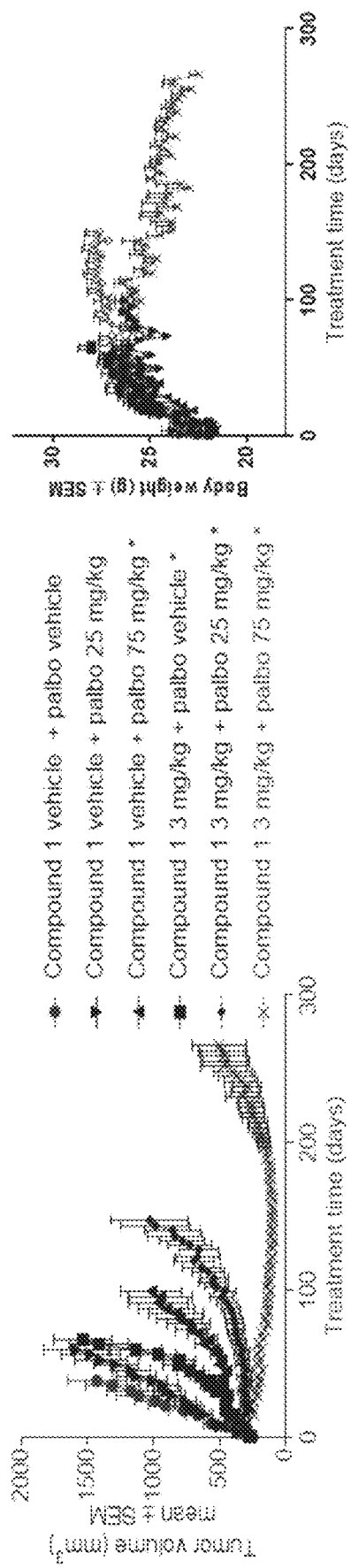
FIG. 8 shows antitumor (left) and body weight effects (right) of oral Compound 1 and palbociclib in female nude mice bearing subcutaneous ST941 breast cancer patient-derived tumor xenografts harboring the ERα$^{WT/Y537S}$. 3 mg/kg Compound 1 and 25 mg/kg or 75 mg/kg palbociclib was given orally QD. Data represent the mean SEM (tumor volume and body weight) (N=8). *P<0.0001 versus vehicle control on Day 38 (two way ANOVA followed by Tukey's test).
Figure 9:
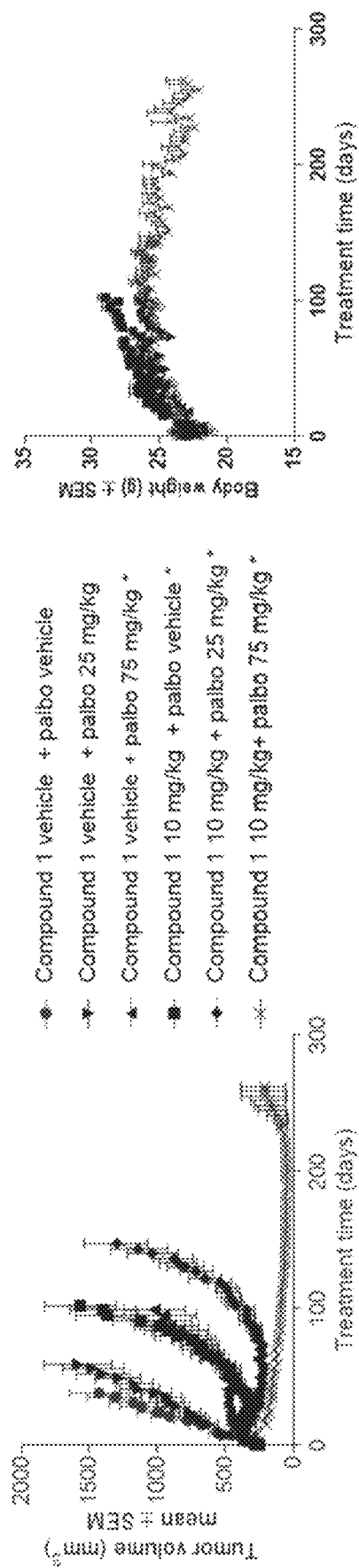
FIG. 9 shows antitumor (left) and body weight effects of oral Compound 1 and palbociclib in female nude mice bearing subcutaneous ST941 breast cancer patient-derived tumor xenografts carrying ERα$^{WT/Y537S}$. 10 mg/kg Compound 1 and 25 mg/kg or 75 mg/kg palbociclib was given orally QD. Data represent the mean SEM (tumor volume and body weight)(N=8). *P<0.0001 versus vehicle control on Day 38 (two way ANOVA followed by Tukey's test).

Example 4—Antitumor and Body Weight Effects of Oral Compound 1 and Palbociclib in Female Nude Mice Bearing Subcutaneous Breast Cancer Patient-Derived Tumor Xenografts Carrying $ER\alpha^{WT/Y537S}$ FIGS. 8 and 9 show the antitumor (left) and the body weight effects (right) of female nude mice orally treated daily with 3 mg/kg and 10 mg/kg Compound 1 as a single agent or in combination with 25 mg/kg and 75 mg/kg palbociclib in the ST941 PDX model bearing an $ER\alpha^{WT/Y537S}$. Palbociclib, as single agent at 25 mg/kg did not significantly inhibit tumor growth with 13% TGI whereas 75 mg/kg significantly inhibited tumor growth with 69% TGI (P<0.0001, FIG. 8 and FIG. 9) without causing SD on day 38. The single agent Compound 1 at 3 mg/kg and 10 mg/kg resulted in significant inhibition of tumor growth with TGI of 50% and 71% (P<0.0001) (FIG. 8 and FIG. 9), respectively, and induced SD in 1/8 mice on day 38.

The combination of 3 mg/kg Compound 1 and 25 mg/kg or 75 mg/kg palbociclib resulted in significant enhancement of tumor growth inhibition relative to vehicle controls with SD being induced in 4/8 and 8/8 mice, respectively, on day 38 (TGI of 80% and 88%, respectively, P<0.0001) (FIG. 8).

The combination of 10 mg/kg Compound 1 and 25 mg/kg or 75 mg/kg palbociclib also resulted in significant enhancement of tumor growth inhibition relative to vehicle controls with SD being induced in 6/8 and 8/8 mice, respectively, on day 38 (TGI of 86% and 91%, respectively, P<0.0001) (FIG. 9). Furthermore, combination of 3 or 10 mg/kg Compound 1 and 75 mg/kg palbociclib enhanced the durability of response with regressions observed with longer treatments.

We claim:

1. A method of treating breast cancer in a patient in need thereof, comprising administering to the patient a combination of an ERα inhibitor selected from the group consisting of (E)-N,N-dimethyl-4-((2-((5-((Z)-4,4,4-trifluoro-1-(3-fluoro-1H-indazol-5-yl)-2-phenylbut-1-en-yl)pyridin-2-yl)oxy)ethyl)amino)but-2-enamide, (E)-4-((2-(4((E)-1-(1H-indazol-5-yl)-2-phenylbut-1-en-1-yl)phenoxy)ethyl)amino)-N,N-dimethylbut-2-enamide, and (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide, or a pharmaceutically acceptable salt thereof and a CDK 4/6 inhibitor or a pharmaceutically acceptable salt thereof.

2. The method of claim 1, wherein the ERα inhibitor is (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide or a pharmaceutically acceptable salt thereof.

3. The method of claim 1, wherein the CDK 4/6 inhibitor is selected from the group consisting of 6-acetyl-8-cyclopentyl-5-methyl-2-{[5-(piperazin-1-yl)pyridin-2yl]amino}pyrido[2,3-d]pyrimidin-7(8H)-one (palbociclib) and pharmaceutically acceptable salts thereof; N-(5-((4-ethylpiperazin-1-yl)methyl)pyridin-2-yl)-5-fluoro-4-(4-fluoro-1-isopropyl-2-methyl-1H -benzo[d]imidazol-6-yl)pyrimidin-2-amine (abemaciclib) and pharmaceutically acceptable salts thereof; and 7-cyclopentyl-2-(5-piperazin-1-yl-pyridin-2-ylamino)-7H-pyrrolo[2,3-d]pyrimidine-6-carboxylic acid dimethylamide (ribociclib); 2'-((5-(4-isopropylpiperazin-1-yl)pyridin-2-yl)amino)-7',8'dihydro-6'H-spiro[cyclohexane1,9' pyrazino[1',2':1,5] pyrrolo[2,3-d]pyrimidin]-6'-one di-hydrochloride; 2'-((5-(4-methylpiperazin-1-yl)pyridin-2-yl)amino)-7',8'-dihydro-6'H-spiro[cyclohexane-1, 9'-pyrazino[1',2':1,5]pyrrolo[2,3-d]pyrimidin]-6'-one (G1T-28); N-(4-piperidinyl)-4-(2,6-dichlorobenzoylamino)-1H-pyrazole-3 carboxamide (AT-7519); 2-Hydroxy-1-[2-[[9-(trans-4-methylcyclohexyl)-9H-pyrido[4',3':4,5]pyrrolo[2,3-d]pyrimidin-2-yl]amino]-7,8-dihydro-1,6-naphthyridin-6 (5H)-yl]ethanone (FLX-925); 2-(2-chlorophenyl)-5,7-dihydroxy-8-((3S,4R)-3-hydroxy-1-methylpiperidin-4-yl)-4H-chromen-4-one (alvocidib) and pharmaceutically acceptable salts thereof.

4. The method of claim 3, wherein the CDK 4/6 inhibitor is palbociclib.

5. The method of claim 3, wherein the CDK 4/6 inhibitor is ribociclib.

6. The method of claim 3, wherein the CDK 4/6 inhibitor is abemaciclib.

7. The method of claim 3, wherein the CDK 4/6 inhibitor is 2'-((5-(4-isopropylpiperazin-1-yl)pyridin-2-yl)amino)-7', 8'dihydro-6'H-spiro[cyclohexane1,9' pyrazino[1',2': 1,5] pyrrolo[2,3-d]pyrimidin]-6'-one di-hydrochloride.

8. The method of claim 3, wherein the CDK 4/6 inhibitor is 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one or a pharmaceutically acceptable salt thereof.

9. The method of claim 8, wherein the 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one or pharmaceutically acceptable salt thereof is administered in a dosage between 190 and 200 mg/m$^2$.

10. The method of claim 3, wherein the CDK 4/6 inhibitor is AT-7519.

11. The method of claim 3, wherein the CDK 4/6 inhibitor is FLX-925.

12. The method of claim 3, wherein the CDK 4/6 inhibitor is alvocidib.

13. The method of claim 1, wherein the ERα inhibitor or pharmaceutically acceptable salt thereof and the CDK 4/6 inhibitor or pharmaceutically acceptable salt thereof are administered as separate formulations.

14. The method of claim 1, wherein the ERα inhibitor or pharmaceutically acceptable salt thereof and the CDK 4/6 inhibitor or pharmaceutically acceptable salt thereof are administered as a single formulation.

15. The method of claim 1, wherein the ERα inhibitor or pharmaceutically acceptable salt thereof and the CDK 4/6 inhibitor or pharmaceutically acceptable salt thereof are administered sequentially.

16. The method of claim 1, wherein the ERα inhibitor or pharmaceutically acceptable salt thereof and the CDK 4/6 inhibitor or pharmaceutically acceptable salt thereof are administered simultaneously.

17. The method of claim 1, wherein the ERα inhibitor is the free base form of the ERα inhibitor.

18. The method of claim 1, wherein the pharmaceutically acceptable salt of the ERα inhibitor is a hydrochloride salt.

19. A pharmaceutical formulation comprising an ERα inhibitor selected from the group consisting of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide, (E)-4-((2-(4((E)-1-(1H-indazol-5-yl)-2-phenylbut-1-en-1-yl)phenoxy)ethyl)amino)-N,N-dimethylbut-2-enamide, and (E)-N,N-dimethyl-4-((2-(4-((E)-4,4,4-trifluoro-1-(3-fluoro-1H-indazol-5-yl)-2-phenylbut-1-en-1-yl)phenoxy)ethyl)amino)but-2-enamide or a pharmaceutically acceptable salt thereof and a CDK 4/6 inhibitor or a pharmaceutically acceptable salt thereof.

20. The pharmaceutical formulation of claim 19, comprising a free base form of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide.

21. The pharmaceutical formulation of claim 19, wherein the ERα inhibitor is a pharmaceutically acceptable salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide.

22. The pharmaceutical formulation of claim 21, wherein the pharmaceutically acceptable salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide is a hydrochloride salt form of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide.

\* \* \* \* \*

SEQUENCE LISTING

<160> NUMBER OF SEQ ID NOS: 2

<210> SEQ ID NO 1
<211> LENGTH: 39
<212> TYPE: DNA

```
<213> ORGANISM: Homo sapiens

<400> SEQUENCE: 1
aagaacgtgg tgccctctc tgacctgctg ctggagatg                              39

<210> SEQ ID NO 2
<211> LENGTH: 39
<212> TYPE: DNA
<213> ORGANISM: Homo sapiens

<400> SEQUENCE: 2
catctccagc agcaggtcag agagggcac cacgttctt                              39
```